(12) United States Patent
Yoshinaga et al.

(10) Patent No.: US 12,245,750 B2
(45) Date of Patent: Mar. 11, 2025

(54) INSERTION DEVICE AND ENDOSCOPE

(71) Applicant: OLYMPUS CORPORATION, Tokyo (JP)

(72) Inventors: Takuto Yoshinaga, Hino (JP); Tsukasa Ota, Hachioji (JP); Wataru Matsuura, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 305 days.

(21) Appl. No.: 17/696,973

(22) Filed: Mar. 17, 2022

(65) Prior Publication Data
US 2022/0202283 A1  Jun. 30, 2022

Related U.S. Application Data

(63) Continuation of application No. PCT/JP2019/036414, filed on Sep. 17, 2019.

(51) Int. Cl.
*A61B 1/012* (2006.01)
*A61B 1/018* (2006.01)

(52) U.S. Cl.
CPC .......... *A61B 1/0125* (2013.01); *A61B 1/018* (2013.01)

(58) Field of Classification Search
CPC .............................. A61B 1/0125; A61B 1/018
See application file for complete search history.

(56) References Cited

U.S. PATENT DOCUMENTS

| 4,245,623 | A | * | 1/1981 | Erb | A61B 17/12099 606/135 |
|---|---|---|---|---|---|
| 5,304,115 | A | * | 4/1994 | Pflueger | A61B 17/22012 606/169 |
| 5,312,399 | A | * | 5/1994 | Hakky | A61B 17/320758 606/14 |
| 6,139,570 | A | * | 10/2000 | Saadat | A61F 7/123 607/105 |
| 6,802,825 | B2 | * | 10/2004 | Ackerman | A61M 25/10 604/528 |
| 8,951,274 | B2 | * | 2/2015 | Adams | A61B 17/42 606/171 |
| 2006/0047185 | A1 | * | 3/2006 | Shener | A61B 1/015 600/156 |

(Continued)

FOREIGN PATENT DOCUMENTS

| JP | 2004249007 A | 9/2004 |
|---|---|---|
| JP | 2004249008 A | 9/2004 |

(Continued)

OTHER PUBLICATIONS

International Search Report dated Dec. 10, 2019 issued in PCT/JP2019/036414.

*Primary Examiner* — Anh Tuan T Nguyen
*Assistant Examiner* — Shankar Raj Ghimire
(74) *Attorney, Agent, or Firm* — Scully, Scott, Murphy & Presser, P.C.

(57) ABSTRACT

An insertion device includes: a tube having a channel hole and a communication hole; a frame member having a tube insertion hole and a forceps channel and disposed to cover a periphery of the communication hole; and a closing member configured to close the channel hole in the tube at a position closer to a proximal end side than the communication hole and having a distal end surface disposed to face the communication hole.

19 Claims, 21 Drawing Sheets

(56) References Cited

U.S. PATENT DOCUMENTS

| | | | |
|---|---|---|---|
| 2006/0293560 A1* | 12/2006 | Nguyen | A61F 6/06 600/104 |
| 2007/0005122 A1* | 1/2007 | Inoue | A61F 2/94 623/1.11 |
| 2007/0100201 A1* | 5/2007 | Komiya | A61B 1/00133 600/106 |
| 2008/0015621 A1* | 1/2008 | Emanuel | A61B 90/30 606/170 |
| 2008/0234715 A1* | 9/2008 | Pesce | A61B 17/32002 606/171 |
| 2009/0171150 A1* | 7/2009 | Lede | G02B 23/26 600/112 |
| 2009/0270897 A1* | 10/2009 | Adams | A61M 1/842 606/170 |
| 2011/0077674 A1* | 3/2011 | Sullivan | A61B 17/3205 606/170 |
| 2011/0118544 A1* | 5/2011 | Adams | A61B 1/015 600/156 |
| 2015/0011827 A1 | 1/2015 | Kinoshita et al. | |
| 2016/0045100 A1* | 2/2016 | Eto | A61B 1/00087 600/106 |
| 2016/0235277 A1* | 8/2016 | Kudo | A61B 1/0014 |
| 2017/0172387 A1* | 6/2017 | Matsui | A61B 1/045 |
| 2020/0397516 A1* | 12/2020 | Hendrick | A61B 1/00133 |
| 2021/0298579 A1* | 9/2021 | Matsushita | A61B 1/00082 |
| 2022/0015613 A1* | 1/2022 | Iizuka | A61B 1/00177 |
| 2022/0296078 A1* | 9/2022 | Suzuki | A61B 1/0052 |

FOREIGN PATENT DOCUMENTS

| | | |
|---|---|---|
| JP | 2004298358 A | 10/2004 |
| JP | 4242172 B2 | 3/2009 |
| JP | 2012170783 A | 9/2012 |
| JP | 2018143583 A | 9/2018 |
| WO | 2013146202 A1 | 10/2013 |
| WO | 2019087550 A1 | 5/2019 |
| WO | 2019123815 A1 | 6/2019 |

* cited by examiner

INSERTION DEVICE AND ENDOSCOPE

CROSS REFERENCE TO RELATED APPLICATION

This application is a continuation application of PCT/JP2019/036414 filed on Sep. 17, 2019, the entire contents of which are incorporated herein by this reference.

BACKGROUND OF THE INVENTION

1. Field of the Invention

The present invention relates to an insertion device including a tube having a hole formed along a longitudinal axis of an insertion portion to be inserted into a subject, and to an endoscope.

2. Description of the Related Art

In recent years, insertion devices, for example, endoscopes, have been widely used in a medical field. Endoscopes allow observation of an organ in a body cavity by inserting an elongated insertion portion into the body cavity, which is a subject, or allow a further detailed observation or various treatments by using a treatment instrument or a known baby endoscope which is inserted into a channel of an endoscope (mother endoscope) when necessary. The mother endoscope refers to an endoscope having a channel into which the insertion portion of the baby endoscope is inserted.

For such a channel, there is a known tube which is provided in an insertion portion and an operation portion of an endoscope and which has a hole through which a treatment instrument, a baby endoscope, a guide wire, or the like can be inserted (hereinafter referred to as "first hole"). There is also a known forceps channel communicating with the tube.

The first hole of the tube extends along a longitudinal axis of the insertion portion (hereinafter simply referred to as "longitudinal axis").

A distal end of the first hole in a direction along the longitudinal axis (hereinafter simply referred to as "distal end") is open as a treatment instrument protrusion opening on a distal end surface of the insertion portion.

Further, a forceps channel communicating with the first hole is branched in a direction intersecting with the longitudinal axis (hereinafter referred to as "intersecting direction") from a portion of the tube which is positioned in the operation portion. The forceps channel is open at a treatment instrument insertion opening provided in the operation portion.

Therefore, such a tube has a configuration where when a treatment instrument, a baby endoscope, a guide wire, and the like are inserted into the tube from the treatment instrument insertion opening, these inserted objects are inserted into the first hole via the forceps channel, and are then caused to protrude from the treatment instrument protrusion opening.

To reduce a diameter of the insertion portion, there is a known configuration where the insertion portion is formed of a multi-lumen tube having a plurality of holes along the longitudinal axis, and one of the plurality of holes is used as the above-mentioned first hole.

In a case where such a multi-lumen tube is used, there is a known configuration where a communication hole is formed on an outer peripheral surface of the multi-lumen tube in the intersecting direction to communicate with the first hole, a frame member having a second hole is disposed to cover a periphery of the communication hole, a proximal end side of the multi-lumen tube in a direction along the longitudinal axis (hereinafter simply referred to as "proximal end side") being inserted into the second hole, and a forceps channel being a third hole is provided in the frame member such that the forceps channel communicates with the communication hole.

As described above, Japanese Patent Application Laid-Open Publication No. 2004-249008 discloses a configuration where the insertion portion is formed of the multi-lumen tube, the communication hole is formed on an outer peripheral surface of one of the plurality of holes of the multi-lumen tube, and a forceps channel is made to communicate with the communication hole in a frame member.

For an endoscope including a small-diameter insertion portion, such as a cholangioscope, a ureteropelvic endoscope, a small intestine endoscope, or a bronchoscope, there is a known technique where a guide wire placed in advance in the body cavity is inserted through the first hole toward the treatment instrument insertion opening from the treatment instrument protrusion opening to insert the insertion portion into a deep part in the body cavity via the guide wire.

In such a case, the guide wire enters the first hole from the treatment instrument protrusion opening and moves through the first hole toward the proximal end side and, thereafter, enters the forceps channel from the communication hole and is then caused to protrude from the treatment instrument insertion opening.

SUMMARY OF THE INVENTION

One aspect of the present invention is directed to an insertion device including: a tube having a first hole and a communication hole, the first hole being formed along a longitudinal axis of an insertion portion inserted into a subject, the communication hole being formed in a direction which intersects with the longitudinal axis, communicating with the first hole, and being open on an outer surface of the tube; a frame member disposed to cover a periphery of the communication hole and having a second hole and a third hole, a proximal end side of the tube being inserted into the second hole, the third hole communicating with the communication hole; and a closing member having a distal end surface at a distal end of the closing member, being inserted into the first hole from a proximal-end-side opening of the first hole, and being configured to close the first hole at a position closer to a proximal end side than the communication hole, the distal end surface of the closing member being positioned at a position closer to a distal end side than a proximal-end-side end portion of the communication hole.

Another aspect of the present invention is directed to an endoscope including: a tube having a first hole and a communication hole, the first hole being formed along a longitudinal axis of an insertion portion inserted into a subject, the communication hole being formed in a direction which intersects with the longitudinal axis, communicating with the first hole, and being open on an outer surface of the tube; an operation portion disposed on a proximal end side of the insertion portion; a frame member disposed to cover a periphery of the communication hole and having a second hole and a third hole, a proximal end side of the tube being inserted into the second hole, the third hole communicating with the communication hole; and a closing member having a distal end surface at a distal end of the closing member, being inserted into the first hole from a proximal-end-side opening of the first hole, and being configured to close the first hole at a position closer to a proximal end side than the communication hole, the distal end surface of the closing member being positioned at a position closer to a distal end side than a proximal-end-side end portion of the communication hole.

DETAILED DESCRIPTION OF THE PREFERRED EMBODIMENT

Hereinafter, an embodiment of the present invention will be described with reference to drawings. In the present embodiment described hereinafter, the description will be made by taking a baby endoscope of an endoscope apparatus including a mother-baby endoscope as an example of an insertion device.

Figure 1:
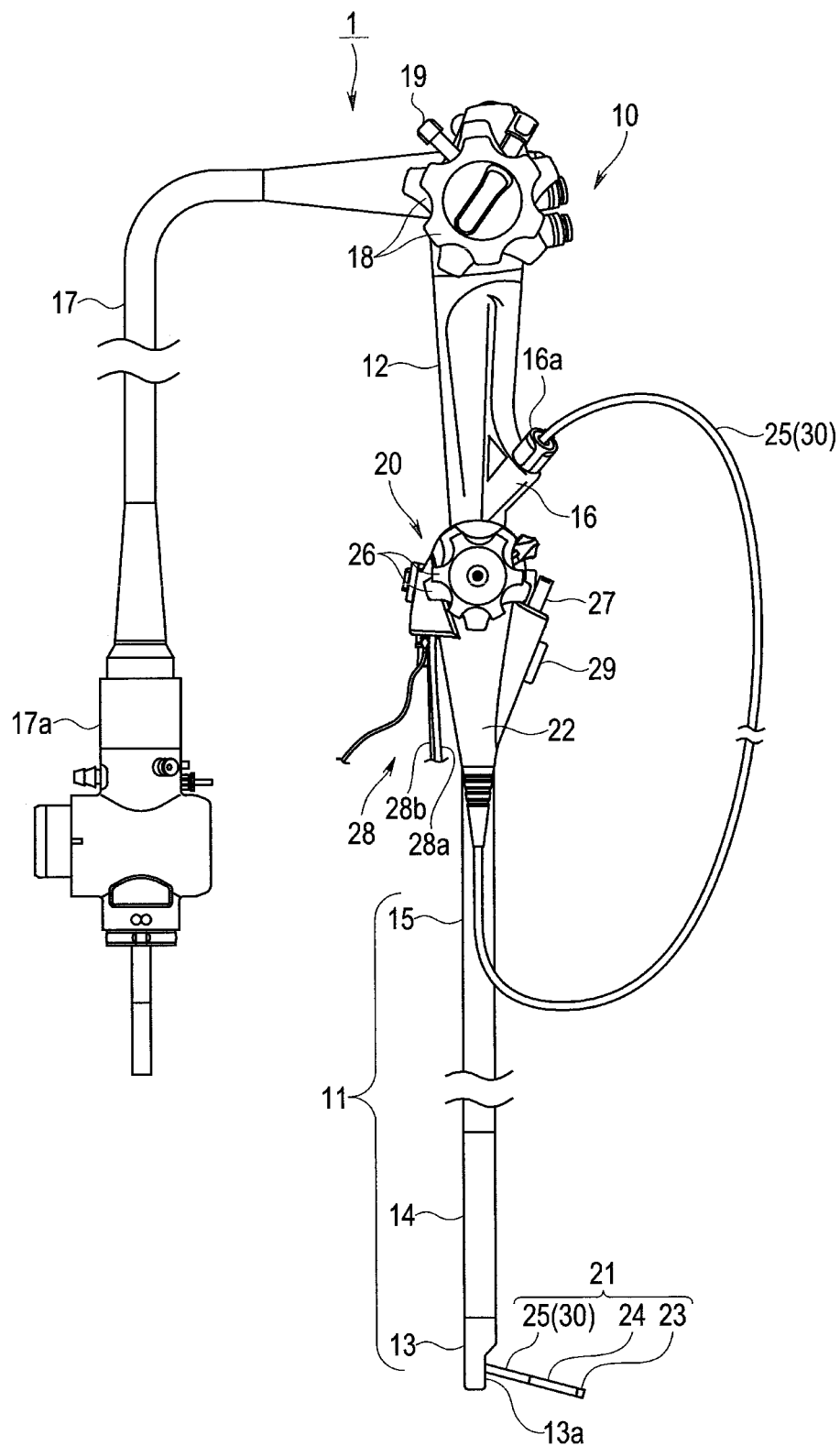
FIG. 1 is a plan view showing an endoscope apparatus including a baby endoscope of the present embodiment and a mother endoscope used in combination with the baby endoscope.
Figure 2:
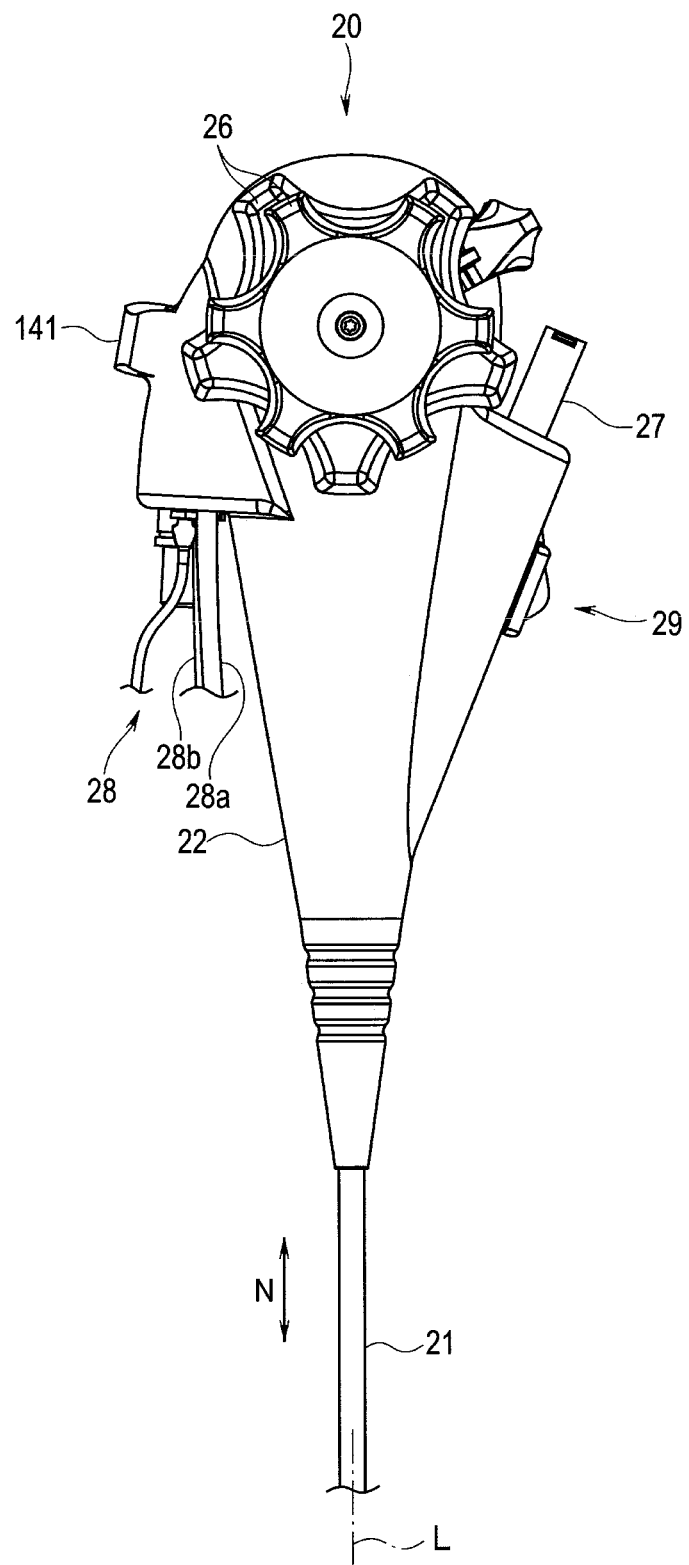
FIG. 2 is a partial plan view of the baby endoscope shown in FIG. 1.

FIG. 1 is a plan view showing an endoscope apparatus including a baby endoscope of the present embodiment and a mother endoscope used in combination with the baby endoscope. FIG. 2 is a partial plan view of the baby endoscope shown in FIG. 1.

Figure 3:
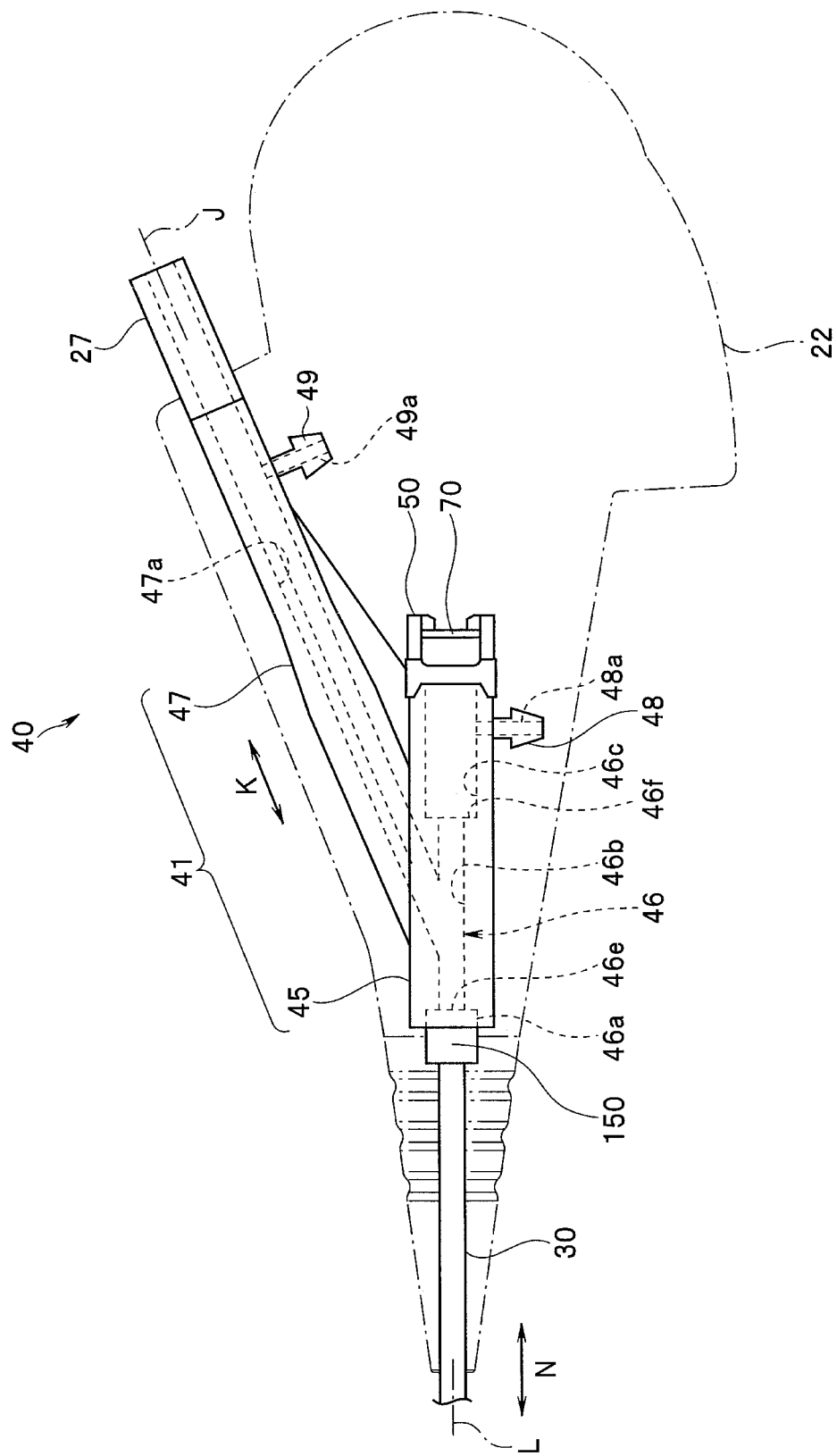
FIG. 3 is a view showing a schematic configuration of a tube module provided in an operation portion shown in FIG. 2.
Figure 4:
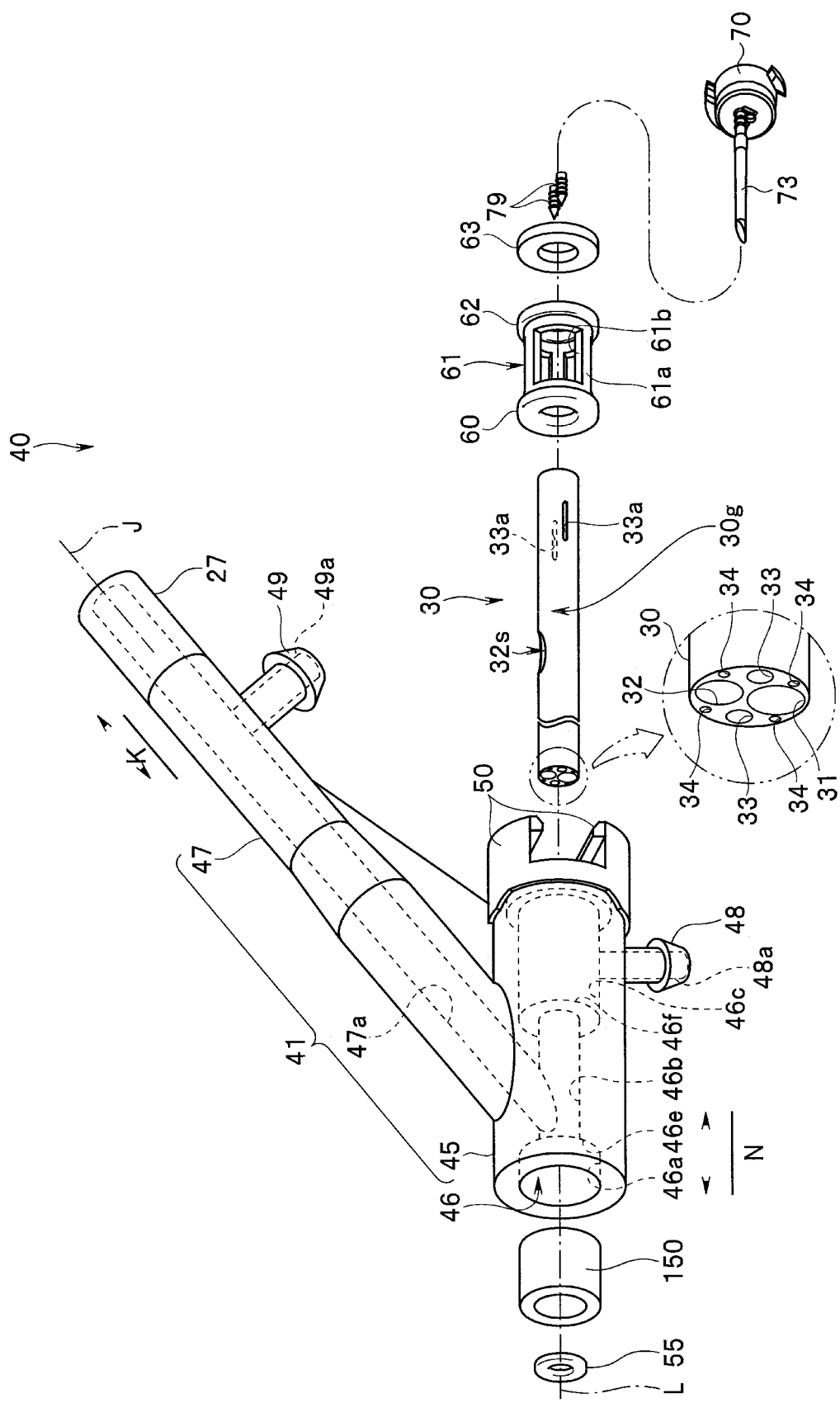
FIG. 4 is an exploded perspective view of the tube module shown in FIG. 3.

FIG. 3 is a view showing a schematic configuration of a tube module provided in an operation portion shown in FIG. 2. FIG. 4 is an exploded perspective view of the tube module shown in FIG. 3.

Figure 5:
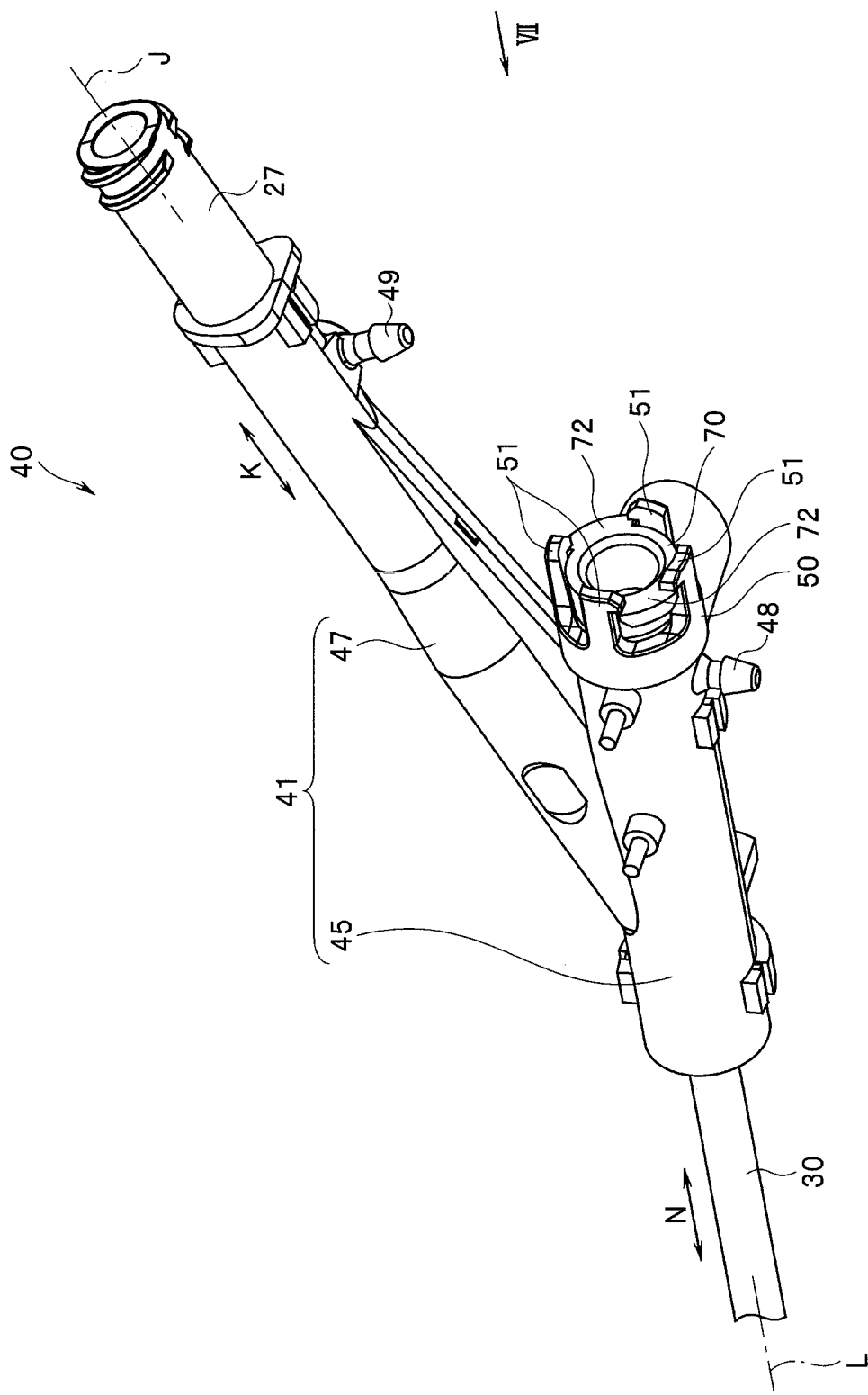
FIG. 5 is a perspective view of the tube module shown in FIG. 3.
Figure 6:
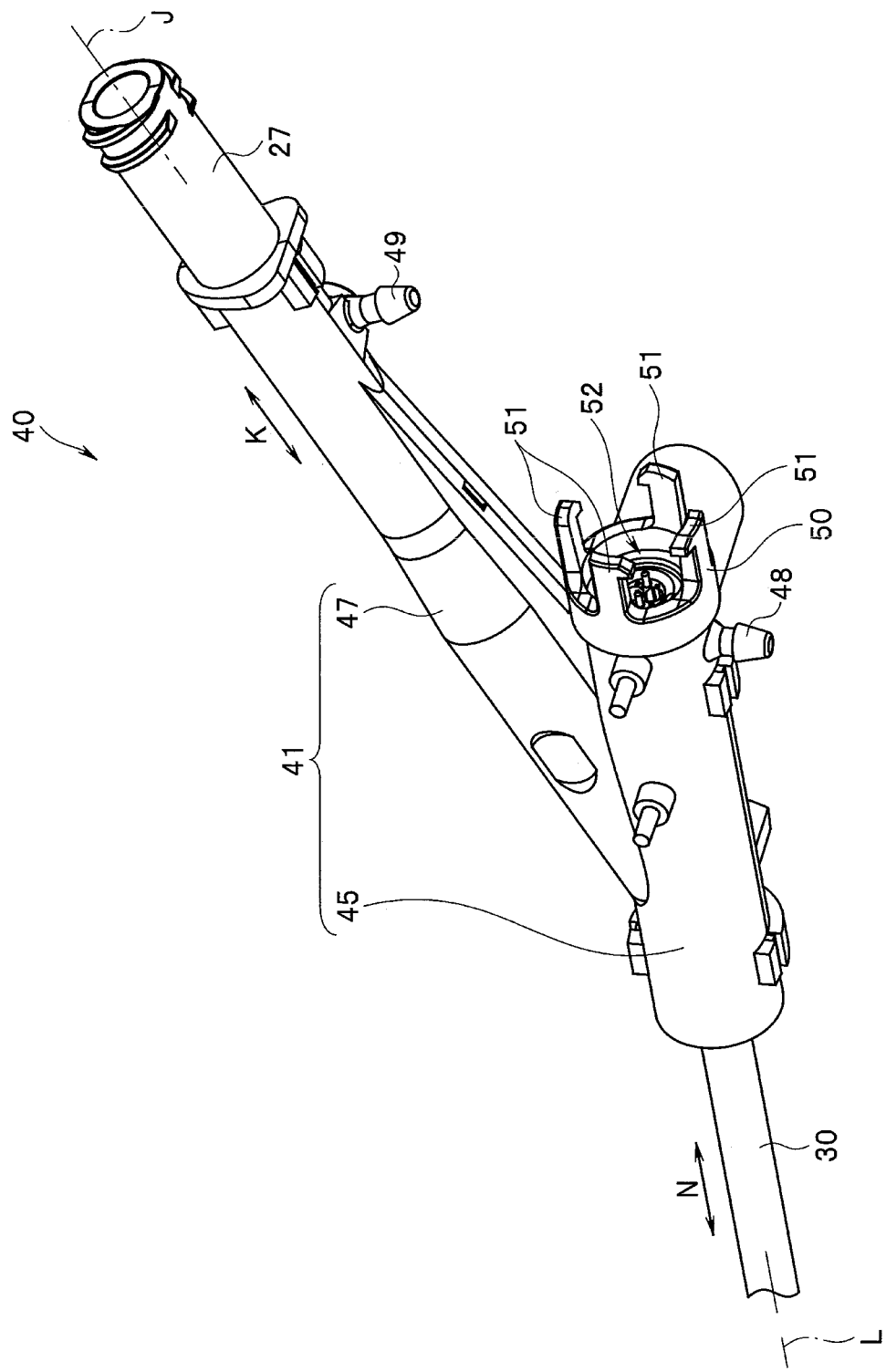
FIG. 6 is a perspective view showing a state where a closing member is removed from the tube module shown in FIG. 5.
Figure 7:
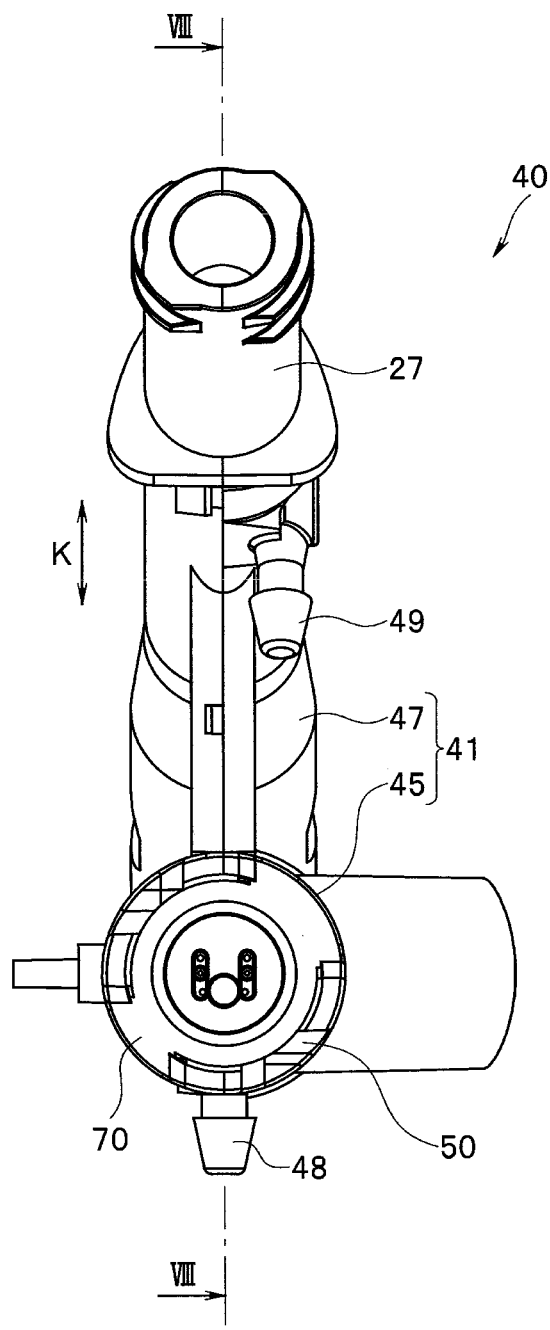
FIG. 7 is a plan view of the tube module shown in FIG. 5 as viewed in a direction VII in FIG. 5.

FIG. 5 is a perspective view of the tube module shown in FIG. 3. FIG. 6 is a perspective view showing a state where a closing member is removed from the tube module shown in FIG. 5. FIG. 7 is a plan view of the tube module shown in FIG. 5 as viewed in a direction VII in FIG. 5.

Figure 8:
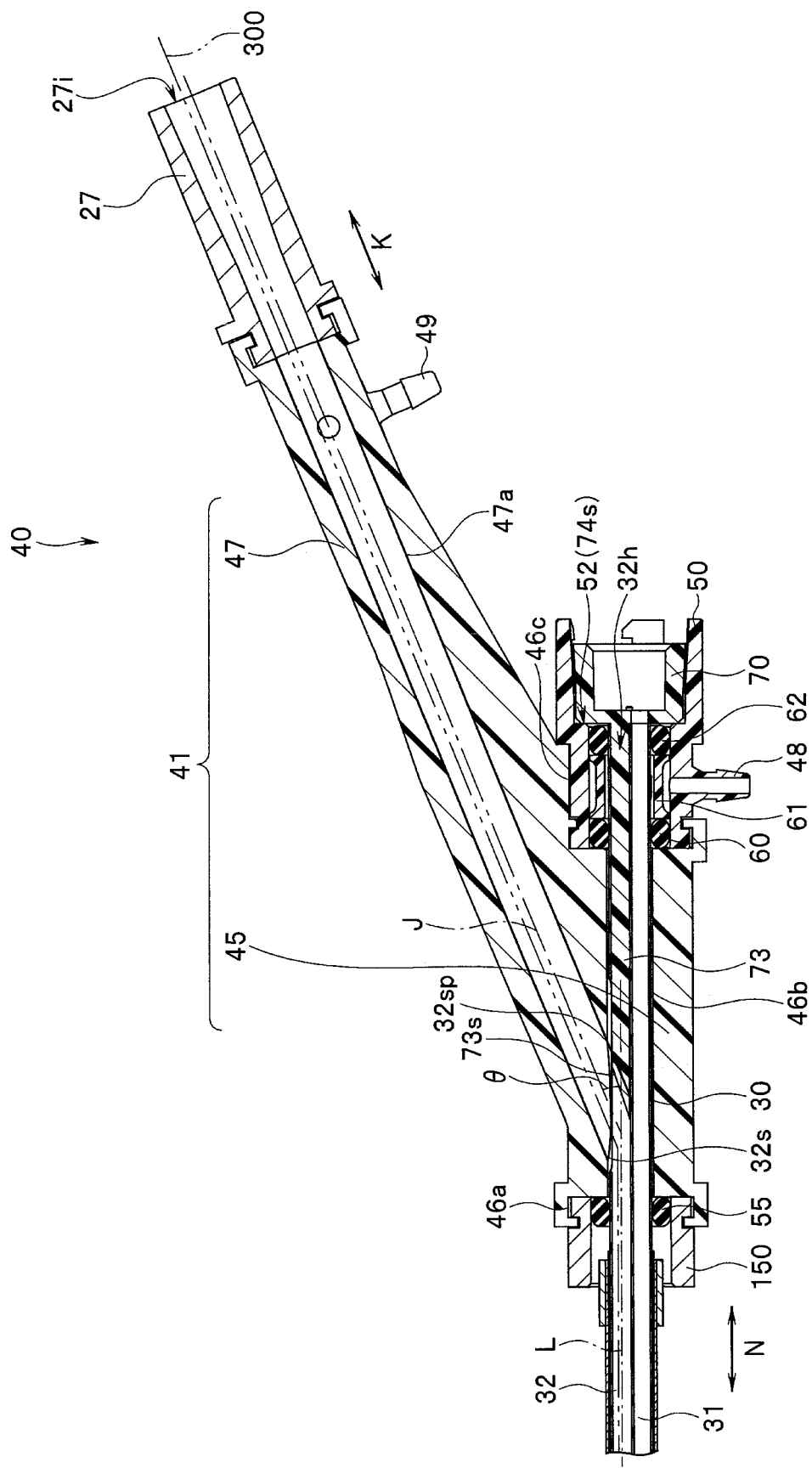
FIG. 8 is a cross-sectional view of the tube module taken along line VIII-VIII in FIG. 7.
Figure 9:
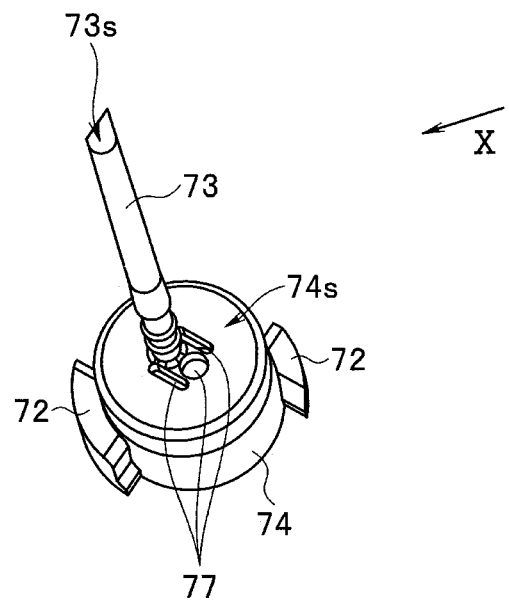
FIG. 9 is an enlarged perspective view of the closing member of the tube module shown in FIG. 4.
Figure 10:
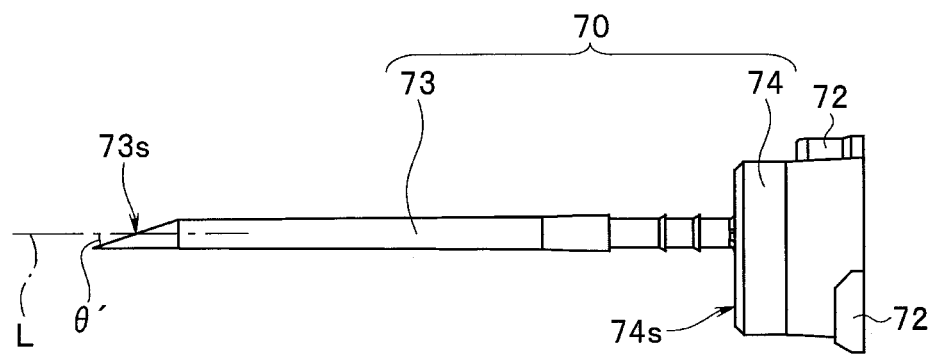
FIG. 10 is a plan view of the closing member shown in FIG. 9 as viewed in a direction X in FIG. 9.

FIG. 8 is a cross-sectional view of the tube module taken along line VIII-VIII in FIG. 7. FIG. 9 is an enlarged perspective view of the closing member of the tube module shown in FIG. 4. FIG. 10 is a plan view of the closing member shown in FIG. 9 as viewed in a direction X in FIG. 9.

As shown in FIG. 1, a main part of an endoscope apparatus 1 is formed by including a mother endoscope 10 and a baby endoscope 20 used in combination with the mother endoscope 10.

A main part of the mother endoscope 10 is formed by including an elongated insertion portion 11, an operation portion 12, a universal cord 17, and an endoscope connector 17a. The elongated insertion portion 11 is to be inserted into a subject. The operation portion 12 is continuously connected with a proximal end side of the insertion portion 11 in a longitudinal direction. The universal cord 17 extends from the operation portion 12. The endoscope connector 17a is provided on an extension end of the universal cord 17, and is detachably mounted on external equipment (not shown in the drawing), such as a light source device.

A main part of the insertion portion 11 is formed by including a distal end portion 13, a bending portion 14, and a flexible tube portion 15 in this order from a distal end side of the insertion portion 11 in a direction of a longitudinal axis.

An image pickup unit and an illumination optical system (neither shown), for example, are provided inside the distal end portion 13. The image pickup unit includes an objective optical system and an image sensor, such as a CCD or a CMOS. The illumination optical system radiates illumination light transmitted through a light guide bundle.

The mother endoscope 10 is, for example, a so-called side-viewing endoscope where optical axes of the image pickup unit and the illumination optical system are inclined by a predetermined angle with respect to the direction of the longitudinal axis of the insertion portion 11.

The distal end portion 13 has an opening portion 13a which is open in a lateral direction. A distal end side of a treatment instrument channel (not shown in the drawing) which is inserted through the insertion portion 11 is made to communicate with the opening portion 13a. The treatment instrument channel is configured such that, in addition to a treatment instrument, a guide wire 300 (see FIG. 8) and the like, an insertion portion 21 described later of the baby endoscope 20 can be inserted through the treatment instrument channel.

The opening portion 13a is provided with a treatment instrument raising base (forceps elevator) not shown in the drawing for raising the treatment instrument, the guide wire 300, the insertion portion 21 of the baby endoscope 20 and the like which are caused to pass through the treatment instrument channel and caused to protrude from the opening portion 13a.

The bending portion 14 is configured to be actively bendable in all directions about an insertion axis including an upward direction, a downward direction, a rightward direction, and a leftward direction (UP-DOWN/RIGHT-LEFT). The flexible tube portion 15 is formed of a tubular member which is passively bendable and having flexibility.

A treatment instrument insertion portion 16 is provided on a distal end side of the operation portion 12, being an insertion portion 11 side of the operation portion 12, and a proximal end side of the treatment instrument channel is made to communicate with the treatment instrument insertion portion 16. A forceps plug 16a is detachably mounted on the treatment instrument insertion portion 16.

A proximal end side of the operation portion 12 is distant from the insertion portion 11, and is provided with a pair of bending operation knobs 18, an operation lever 19, and the like. The pair of bending operation knobs 18 is provided to perform a bending operation of the bending portion 14. The operation lever 19 is provided to operate the treatment instrument raising base.

In the above-mentioned description, a case where the mother endoscope 10 is a side-viewing endoscope is taken as an example. However, the mother endoscope 10 may be a so-called front-view type endoscope that observes a region in front of the distal end portion 13 in the direction of the longitudinal axis.

A main part of the baby endoscope 20 is formed by including the elongated insertion portion 21 and an operation portion 22. The elongated insertion portion 21 is to be inserted into the subject. The operation portion 22 is continuously connected with a proximal end side of the insertion portion 21.

A main part of the insertion portion 21 is formed by including a distal end portion 23, a bending portion 24, and a flexible tube portion 25 in this order from a distal end side of the insertion portion 21 (hereinafter simply referred to as "distal end side") in a direction N along a longitudinal axis L (see FIG. 2) (hereinafter simply referred to as "direction N").

In the same manner as the above-mentioned mother endoscope 10, an image pickup unit and an illumination optical system (neither shown), for example, are provided inside the distal end portion 23. The illumination optical system irradiates the subject with illumination light.

In the present embodiment, the description will be made by taking a so-called front-view type endoscope as an example of the baby endoscope 20. In the front-view type endoscope, optical axes of the above-mentioned image pickup unit and illumination optical system are set along the longitudinal axis L.

A distal end surface of the distal end portion 23 is provided with an observation window of the image pickup unit, an illumination window of the illumination optical system, a water feeding nozzle, various openings, and the like.

The bending portion 24 is configured to be actively bendable in four directions, being the upward direction, the downward direction, the leftward direction, or the rightward direction, for example, with an operation of bending operation knobs 26 described later, which are provided on the operation portion 22.

The flexible tube portion 25 is formed of a tubular member which is passively bendable and having flexibility. In the present embodiment, the flexible tube portion 25 is formed of a tube 30 having flexibility. The tube 30 may be provided in the flexible tube portion 25.

The tube 30 has a hole in the inside of the tube 30, and the hole extends from a distal end side to a proximal end side of the tube 30 along the longitudinal axis L. The tube 30 may be a so-called multi-lumen tube having at least two holes.

Hereinafter, in the present embodiment, the description will be made by taking a case where the tube 30 is a multi-lumen tube as an example.

Specifically, as shown in FIG. 4, in the present embodiment, the tube 30 is a multi-lumen tube having eight holes, that is, an observation hole 31, a channel hole 32, a pair of water feeding holes 33, and four wire insertion holes 34. For example, an image guide bundle (or a signal line of the image pickup unit), a light guide bundle, and the like are inserted through the observation hole 31. The channel hole 32 is a first hole serving as both a suction channel and a treatment instrument insertion channel. Four wires not shown in the drawing which are connected to the bending operation knobs 26 are inserted through the four wire insertion holes 34.

The number of holes formed in the tube 30 is not limited to eight, and needless to say, the tube 30 may have any number of holes.

A configuration may be adopted where the flexible tube portion 25 is formed of the tube 30 and the bending portion 24 is also formed of the tube 30.

Returning to FIG. 1, the operation portion 22 is provided with the pair of bending operation knobs 26 and a treatment instrument insertion pipe sleeve 27. The pair of bending operation knobs 26 is provided to perform an bending operation of the bending portion 24. The treatment instrument insertion pipe sleeve 27 is provided to insert the treatment instrument and the guide wire 300 (see FIG. 8) into the channel hole 32.

Cables/tubes 28 including the image guide bundle, the light guide bundle, a suction tube 28a, a water feeding tube 28b and the like extend from the operation portion 22.

In the baby endoscope 20 of the present embodiment, the above-mentioned image pickup unit may be provided in the operation portion 22. In this case, a signal cable connected to the image pickup unit extends from the operation portion 22 in place of the image guide bundle.

As shown in FIG. 2, one end of a fixing band 29 is fixed to the operation portion 22. The fixing band 29 is provided to fix the operation portion 22 to the operation portion 12 of the mother endoscope 10. A fixing band hook 141 is also provided on the operation portion 22. In fixing the operation portion 22 to the operation portion 12 of the mother endoscope 10, the fixing band 29 is wound around the operation portion 12, and the other end of the fixing band 29 is locked to the fixing band hook 141.

Configurations of the fixing band 29 and the fixing band hook 141 and a method for fixing the operation portion 22 to the operation portion 12 will be described later in the description made with reference to FIG. 11 to FIG. 19.

On the proximal end side of the tube 30, the treatment instrument insertion pipe sleeve 27 and the suction tube 28a are made to communicate with the channel hole 32. Further, the water feeding tube 28b is made to communicate with the pair of water feeding holes 33.

To achieve these communications, in the present embodiment, a tube module 40 is provided on the proximal end side of the tube 30 as shown in FIG. 3.

As shown in FIG. 3 to FIG. 8, the tube module 40 includes a frame member 41. A main part of the frame member 41 is formed by including a body portion 45 and a branch portion 47 which communicates with the body portion 45.

The entire frame member 41 may be integrally formed by a 3D printer, for example. Alternatively, the frame member 41 may be formed by combining two parts each of which is formed by molding.

The frame member 41 is made of a material having high slidability, such as polycarbonate, polypropylene, polyethylene, or polyacetal. Provided that a material for forming the frame member 41 has high slidability, the material is not limited to these materials.

In the operation portion 22, the frame member 41 is held to cover a periphery of a communication hole 32s which is formed on an outer peripheral surface 30g of the tube 30 (see FIG. 4). With such a configuration, the proximal end side of the tube 30 (that is, the proximal end side of the insertion portion 21) is continuously connected with the operation portion 22.

As shown in FIG. 4, the proximal end side of the tube 30 has the communication hole 32s and a pair of water feeding communication holes 33a.

Specifically, the communication hole 32s communicates with the channel hole 32 and is formed in an intersecting direction K.

Each water feeding communication hole 33a is a hole which makes an inner peripheral surface of each water feeding hole 33 communicate with the outer peripheral surface 30g of the tube 30 in a direction substantially orthogonal to the direction N.

The communication hole 32s and each water feeding communication hole 33a are formed in a region on the proximal end side of the tube 30 at positions displaced from each other in the direction N.

Specifically, the communication hole 32s is formed at a position displaced further toward the distal end side relative to the pair of water feeding communication holes 33a.

In the present embodiment, the description is made by taking, as an example, the configuration where the pair of water feeding communication holes 33a is formed in the tube 30 corresponding to the pair of water feeding holes 33. However, the configuration is not limited to such a configuration. In the case where one water feeding hole 33 is formed, it is sufficient to form the water feeding communication hole 33a in the tube 30 at one location.

In the case where three or more water feeding holes 33 are formed, it is sufficient to form the water feeding communication holes 33a in the tube 30 at three or more locations.

As shown in FIG. 4, the body portion 45 is formed to have a cylindrical shape along the longitudinal axis L. A tube insertion hole 46 being a second hole is formed in the body portion 45 in the direction N. The proximal end side of the tube 30 is inserted into the second hole.

The tube insertion hole 46 is formed of a stepped through hole having an inner peripheral surface with an inner diameter larger than the outer peripheral surface 30g of the tube 30.

Specifically, as shown in FIG. 3 and FIG. 4, a main part of the tube insertion hole 46 is formed by including, in this order from a distal end side of the tube insertion hole 46, a first insertion hole portion 46a, a second insertion hole portion 46b, and a third insertion hole portion 46c, for example. The first insertion hole portion 46a has an inner diameter sufficiently larger than an outer diameter of the tube 30. The second insertion hole portion 46b has an inner diameter smaller than the inner diameter of the first insertion hole portion 46a (but is slightly larger than the outer diameter of the tube 30). The third insertion hole portion 46c has an inner diameter larger than the inner diameter of the second insertion hole portion 46b (for example, a diameter equal to a diameter of the first insertion hole portion 46a).

Further, the branch portion 47 is integrally formed with the body portion 45. The branch portion 47 extends in the intersecting direction K. The treatment instrument insertion pipe sleeve 27 is coupled with an extension end of the branch portion 47 in the intersecting direction K.

A suction branch tube 49 is integrally formed with the branch portion 47 at an intermediate position in the intersecting direction K. The suction tube 28a is connectable to the suction branch tube 49.

A forceps channel 47a being a third hole is formed in the branch portion 47 and the treatment instrument insertion pipe sleeve 27.

The forceps channel 47a communicates with the second insertion hole portion 46b. As shown in FIG. 8, a center axis J of the forceps channel 47a forms an acute angle θ with the longitudinal axis L.

A suction branch conduit 49a of the suction branch tube 49 is branched from the forceps channel 47a at the intermediate position in the intersecting direction K.

On a distal end side of the body portion 45, the first insertion hole portion 46a forms a portion in which a cylindrical connection pipe sleeve 150 is fitted from a distal end side of the first insertion hole portion 46a for engagement.

The connection pipe sleeve 150 holds an O-shaped ring 55 which water-tightly holds the outer peripheral surface 30g of the tube 30 and the inner peripheral surface of the tube insertion hole 46.

The second insertion hole portion 46b is formed with a diameter smaller than the inner diameter of the first insertion hole portion 46a, so that a first stopper portion 46e is formed at a proximal end of the first insertion hole portion 46a in the direction N (hereinafter simply referred to as "proximal end"). The first stopper portion 46e protrudes inward from the tube insertion hole 46.

The O-shaped ring 55 is brought into contact with the first stopper portion 46e, so that the movement of the O-shaped ring 55 toward the proximal end side is restricted. The positioning of the O-shaped ring 55 in the connection pipe sleeve 150 is performed in this manner The O-shaped ring 55 is brought into close contact with the outer peripheral surface 30g of the tube 30 and an inner peripheral surface of the connection pipe sleeve 150 and hence, a gap between the tube 30 and the connection pipe sleeve 150 is air-tightly and liquid-tightly sealed by each O-shaped ring 55.

The second insertion hole portion 46b is provided corresponding to the communication hole 32s which is open on the outer peripheral surface 30g of the tube 30.

The positioning of the tube 30 in the tube insertion hole 46 is performed such that the communication hole 32s is positioned at the second insertion hole portion 46b. Therefore, the channel hole 32 formed in the tube 30 is made to communicate with the forceps channel 47a via the communication hole 32s.

The third insertion hole portion 46c is provided corresponding to the water feeding communication holes 33a which are open on the outer peripheral surface 30g of the tube 30.

As shown in FIG. 5, FIG. 7, and FIG. 8, a locking pawl portion (hereinafter simply referred to as "pawl portion") 50 having four pawls 51 is inserted into the third insertion hole portion 46c. A water feeding branch tube 48 is integrally formed with the pawl portion 50.

A water feeding branch conduit 48a communicating with the third insertion hole portion 46c is formed in the water feeding branch tube 48. The water feeding tube 28b is connectable to the water feeding branch tube 48.

An O-shaped ring 60, a cylindrical spacer 61, an O-shaped ring 62, and an annular adjusting ring 63 are inserted into the pawl portion 50 in this order from a proximal end side of the body portion 45.

The second insertion hole portion 46b is formed with a diameter smaller than the inner diameter of the third insertion hole portion 46c, so that a second stopper portion 46f is formed at a distal end of the third insertion hole portion 46c. The second stopper portion 46f protrudes inward from the tube insertion hole 46.

The O-shaped ring 60 and the pawl portion 50 are brought into contact with the second stopper portion 46f, so that the movement of the O-shaped ring 60 and the pawl portion 50 toward the distal end side is restricted. The positioning of the pawl portion 50, the O-shaped ring 60, the spacer 61, the O-shaped ring 62, and the adjusting ring 63 in the third insertion hole portion 46c is performed in this manner Specifically, the O-shaped ring 60 is brought into contact with the second stopper portion 46f, thus being positioned in the third insertion hole portion 46c at a position closer to the distal end side than the water feeding communication holes 33a and the water feeding branch conduit 48a.

The O-shaped ring 60 which is positioned as described above is brought into close contact with the outer peripheral surface 30g of the tube 30 and an inner peripheral surface of the pawl portion 50. Therefore, at the position closer to the distal end side than the water feeding communication holes 33a and the water feeding branch conduit 48a, a gap between the outer peripheral surface 30g of the tube 30 and the pawl portion 50 is air-tightly and liquid-tightly sealed by the O-shaped ring 60.

The spacer 61 is brought into contact with the O-shaped ring 60 (that is, the spacer 61 is brought into contact with the second stopper portion 46f via the O-shaped ring 60), thus being positioned in the third insertion hole portion 46c at a position which corresponds to the water feeding communication holes 33a and an opening portion of the water feeding branch conduit 48a.

The spacer 61 includes a substantially cylindrical wall portion 61a, which is disposed between the tube 30 and the third insertion hole portion 46c (the tube insertion hole 46), with a predetermined gap formed between the wall portion 61a and the tube 30 and with a predetermined gap formed between the wall portion 61a and the third insertion hole portion 46c.

Communication holes 61b are formed in the wall portion 61a of the spacer 61. The communication holes 61b make an inner surface side and an outer surface side of the wall portion 61a communicate with each other.

The spacer 61 having such communication holes 61b is disposed at a position which corresponds to the water feeding communication holes 33a and the opening portion of the water feeding branch conduit 48a and hence, each of the pair of water feeding holes 33 formed in the tube 30 is made to communicate with the water feeding branch conduit 48a.

The O-shaped ring 62 is brought into contact with the spacer 61 (that is, the O-shaped ring 62 is brought into contact with the second stopper portion 46f via the O-shaped ring 60 and the spacer 61), thus being positioned in the pawl portion 50 at a position closer to the proximal end side than the water feeding communication holes 33a and the water feeding branch conduit 48a.

The O-shaped ring 62 which is positioned as described above is brought into close contact with the outer peripheral surface 30g of the tube 30 and the inner peripheral surface of the pawl portion 50. Therefore, at the position closer to the proximal end side than the water feeding communication holes 33a and the water feeding branch conduit 48a, a gap between the outer peripheral surface 30g of the tube 30 and the pawl portion 50 is air-tightly and liquid-tightly sealed by the O-shaped ring 62. The O-shaped ring 60, the spacer 61, and the O-shaped ring 62 are integrally formed in advance.

The adjusting ring 63 is brought into contact with the O-shaped ring 62 (that is, the adjusting ring 63 is brought into contact with the second stopper portion 46f via the O-shaped ring 60, the spacer 61, and the O-shaped ring 62), thus being positioned in the pawl portion 50 at a position close to a proximal end side of the pawl portion 50.

A closing member 70 is fitted and held in the pawl portion 50 to close a proximal end of the pawl portion 50.

As shown in FIG. 9 and FIG. 10, the closing member 70 includes a lid body 74 and a pin-shaped sealing member 73. The lid body 74 is provided to close the pawl portion 50. The sealing member 73 extends toward the distal end side from a distal end surface 74s of the lid body 74.

When the lid body 74 is fitted in the pawl portion 50 to close the proximal end of the pawl portion 50, as shown in FIG. 8, the sealing member 73 is inserted into the channel hole 32 toward the distal end side from a proximal-end-side opening 32h of the channel hole 32, thus sealing a portion of the channel hole 32 at a position closer to the proximal end side than the communication hole 32s.

With such a configuration, when a suction operation is performed from the suction branch conduit 49a via the forceps channel 47a, the communication hole 32s, and the channel hole 32, air tightness is ensured by the sealing member 73 on a proximal end side of the channel hole 32.

The sealing member 73 is made of a material having a rigidity higher than a rigidity of a material used for forming the tube 30, thus preventing deformation of the sealing member 73 even when the sealing member 73 is pushed by a guide wire toward the proximal end side. Examples of such a material include polycarbonate, polypropylene, polyethylene, and polyacetal.

A distal end surface 73s disposed at a distal end of the sealing member 73 is positioned in the channel hole 32 in a state of being exposed to the communication hole 32s so as to face the communication hole 32s.

When the lid body 74 closes the proximal end of the pawl portion 50, a pin-shaped sealing member 79 is inserted into a proximal end of each water feeding hole 33. With such a configuration, the proximal end of each water feeding hole 33 is sealed by the sealing member 79. The sealing member 79 may be integrally formed with the distal end surface 74s of the lid body 74.

Through holes 77 are formed in the lid body 74 at positions which correspond to the observation hole 31 and the respective wire insertion holes 34. The through holes 77 penetrate through the lid body 74 in the longitudinal axis L.

When the lid body 74 closes the proximal end of the pawl portion 50, the image guide bundle and the light guide bundle can be inserted through the observation hole 31 via the through hole 77 and wires can be inserted through the respective wire insertion holes 34 via the through holes 77.

Flange portions 72 are provided on an outer peripheral surface of the lid body 74. The flange portions 72 are locking portions which protrude outward in a radial direction.

When the flange portions 72 are locked to the pawls 51 of the pawl portion 50 as shown in FIG. 5, the lid body 74 is held in the pawl portion 50 in a state where a position of the lid body 74 in a rotational direction with respect to the pawl portion 50 is restricted.

The pawl portion 50 may be integrally formed with the body portion 45.

As shown in FIG. 8, the lid body 74 is fitted into the pawl portion 50 until the distal end surface 74s abuts against a stepped portion 52 in the pawl portion 50. The stepped portion 52 is formed on the inner peripheral surface of the pawl portion 50 at a proximal end of the third insertion hole portion 46c in the direction N along the longitudinal axis.

In fitting the lid body 74 into the pawl portion 50, the tube 30 is pushed toward the distal end side by the closing member 70 in the pawl portion 50, so that positioning of the proximal end position of the tube 30 with respect to the body portion 45 is automatically performed along the longitudinal axis L.

With such an operation, the positioning of the tube 30 within the pawl portions 50 along the longitudinal axis L is automatically performed. Therefore, the communication hole 32s is disposed in the second insertion hole portion 46b and the water feeding communication holes 33a are disposed in the third insertion hole portion 46c.

With the above-mentioned positioning of the closing member 70 in the rotational direction which is performed by locking the flange portions 72 to the pawls 51, the positioning of the tube 30 in the tube insertion hole 46 in the rotational direction about the longitudinal axis L is automatically performed. Therefore, the communication hole 32s is disposed in the second insertion hole portion 46b at a position which matches with the forceps channel 47a.

The O-shaped ring 60, the spacer 61, and the O-shaped ring 62 are sandwiched between the second stopper portion 46f and the lid body 74 via the adjusting ring 63, so that the O-shaped ring 60, the spacer 61, and the O-shaped ring 62 are held in a state of being positioned at predetermined positions which use the second stopper portion 46f as a reference.

The sealing member 73 is inserted into the channel hole 32 from the proximal-end-side opening 32h to seal the channel hole 32 at a position closer to the proximal end side than the communication hole 32s. The sealing member 73 is positioned such that the distal end surface 73s faces the communication hole 32s.

Specifically, the sealing member 73 is positioned such that the entire distal end surface 73s is positioned at least at a position closer to the distal end side than a proximal end 32sp of the communication hole 32s. The proximal end 32sp is a proximal-end-side end portion in the direction N of a portion where the communication hole 32s merges with the channel hole 32.

The distal end surface 73s faces the communication hole 32s in the channel hole 32 and, as shown in FIG. 8, is formed into a shape which smoothly connects the channel hole 32 with the forceps channel 47a in a state where the distal end surface 73s is positioned.

Specifically, the distal end surface 73s is formed such that at least a portion of the distal end surface 73s is parallel to the center axis J. Alternatively, the distal end surface 73s is formed as an inclined surface with an angle θ' formed between at least the portion of the distal end surface 73s and the longitudinal axis L being smaller than an angle formed between the center axis J and the longitudinal axis L.

The shape of the distal end surface 73s which smoothly connects the channel hole 32 with the forceps channel 47a is not limited to an inclined surface, and may be a curved surface or the like.

Other configurations of the tube module 40 are equal to configurations of a conventional tube module.

In the present embodiment, it is described that the sealing member 73 seals the channel hole 32 at a position closer to the proximal end side than the communication hole 32s, and is positioned such that the distal end surface 73s formed as an inclined surface faces the communication hole 32s.

It is also described that a portion of the distal end surface 73s is formed parallel to the center axis J or the angle θ' formed between the portion of the distal end surface 73s and the longitudinal axis L is set to be smaller than the angle formed between the center axis J and the longitudinal axis L.

With such a configuration, when the guide wire 300 is inserted into the channel hole 32 from the distal end side to the proximal end side of the channel hole 32 to cause the guide wire 300 to enter the forceps channel 47a via the communication hole 32s, there is no possibility that the guide wire 300 may be caught by a periphery of the communication hole 32s due to the distal end surface 73s.

Therefore, it is possible to smoothly guide the guide wire 300 from the channel hole 32 to the forceps channel 47a.

Such a configuration allows an insertion operation to be smoothly performed in inserting the insertion portion 21 of the baby endoscope 20 into a body cavity via the guide wire 300 inserted into the treatment instrument channel of the mother endoscope 10.

Accordingly, it is possible to provide the baby endoscope 20 having the configuration which allows the guide wire 300 to smoothly enter the forceps channel 47a from the first hole 32 of the tube 30 via the communication hole 32s.

In the above-mentioned present embodiment, the description has been made by taking the baby endoscope 20 as an example of the insertion device. However, the insertion device is not limited to the baby endoscope 20, and may be the mother endoscope 10. Specifically, the insertion device may be the tube module of the mother endoscope 10. The insertion device may also be another treatment instrument including the tube 30 which is inserted into a body cavity via the guide wire 300.

In the above-mentioned present embodiment, the description has been made by taking, as an example, the case where the insertion portion 21 is formed of the tube 30 and the tube 30 is a multi-lumen tube. However, the configuration is not limited to the above, and a configuration may also be adopted where the tube 30 has only one hole.

Next, the description will be made with reference to FIG. 11 to FIG. 19 for a configuration of fixing the operation portion 22 of the baby endoscope 20 to the operation portion 12 of the mother endoscope 10 by using the fixing band 29.

Figure 11:
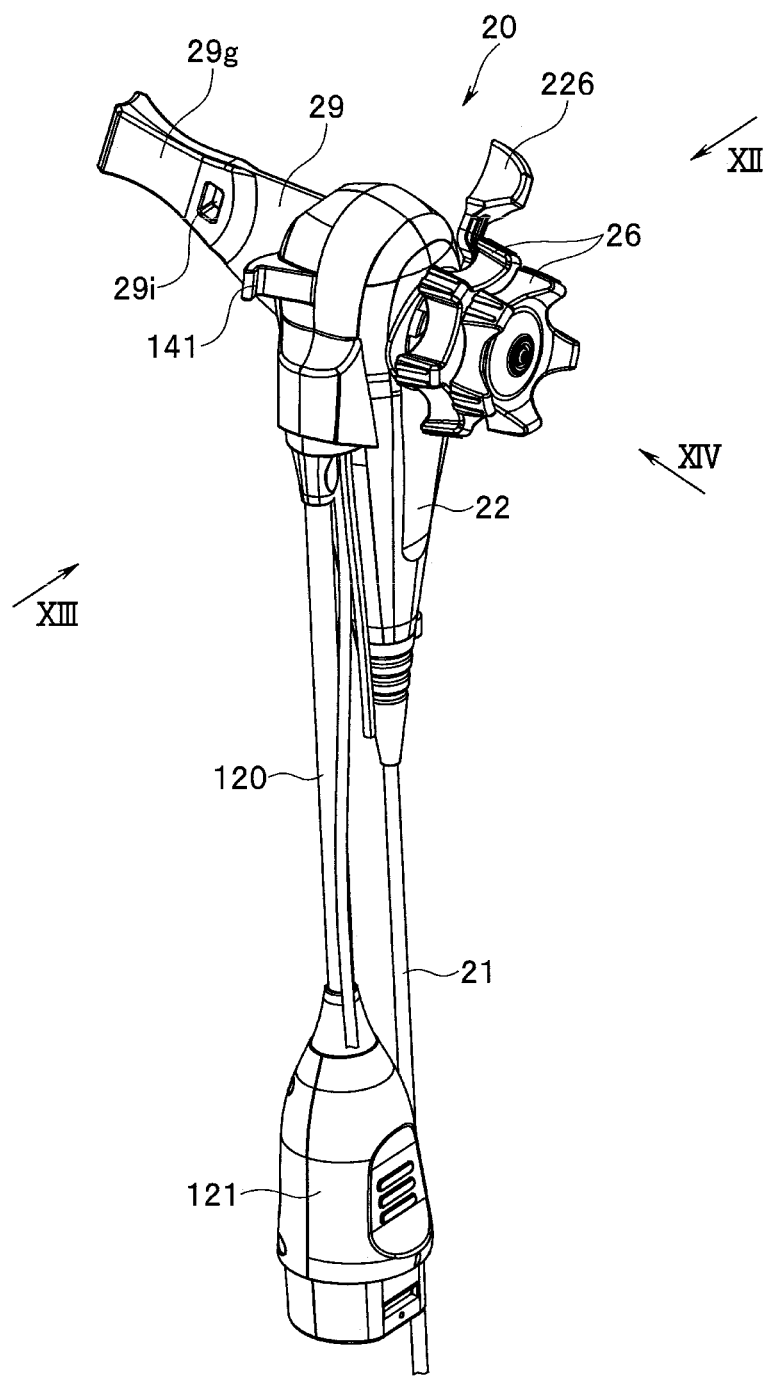
FIG. 11 is an enlarged perspective view of the baby endoscope shown in FIG. 2.
Figure 12:
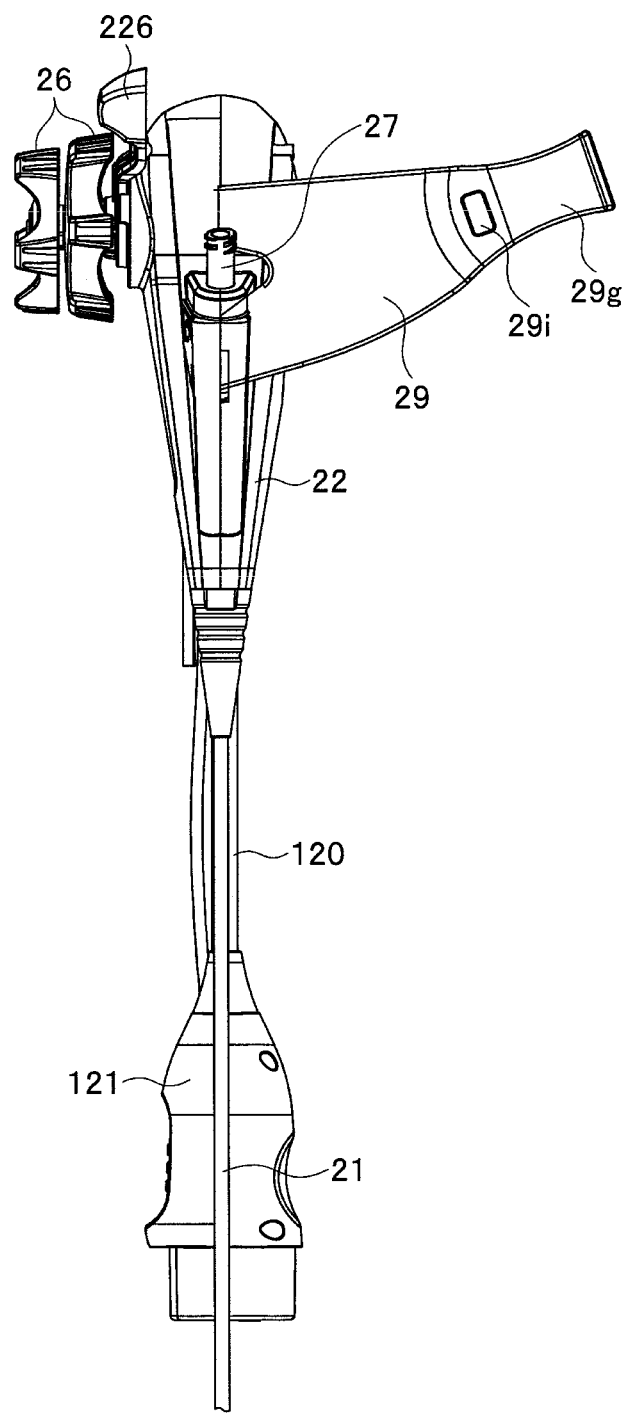
FIG. 12 is a side view of the baby endoscope shown in FIG. 11 as viewed in a direction XII in FIG. 11.
Figure 13:
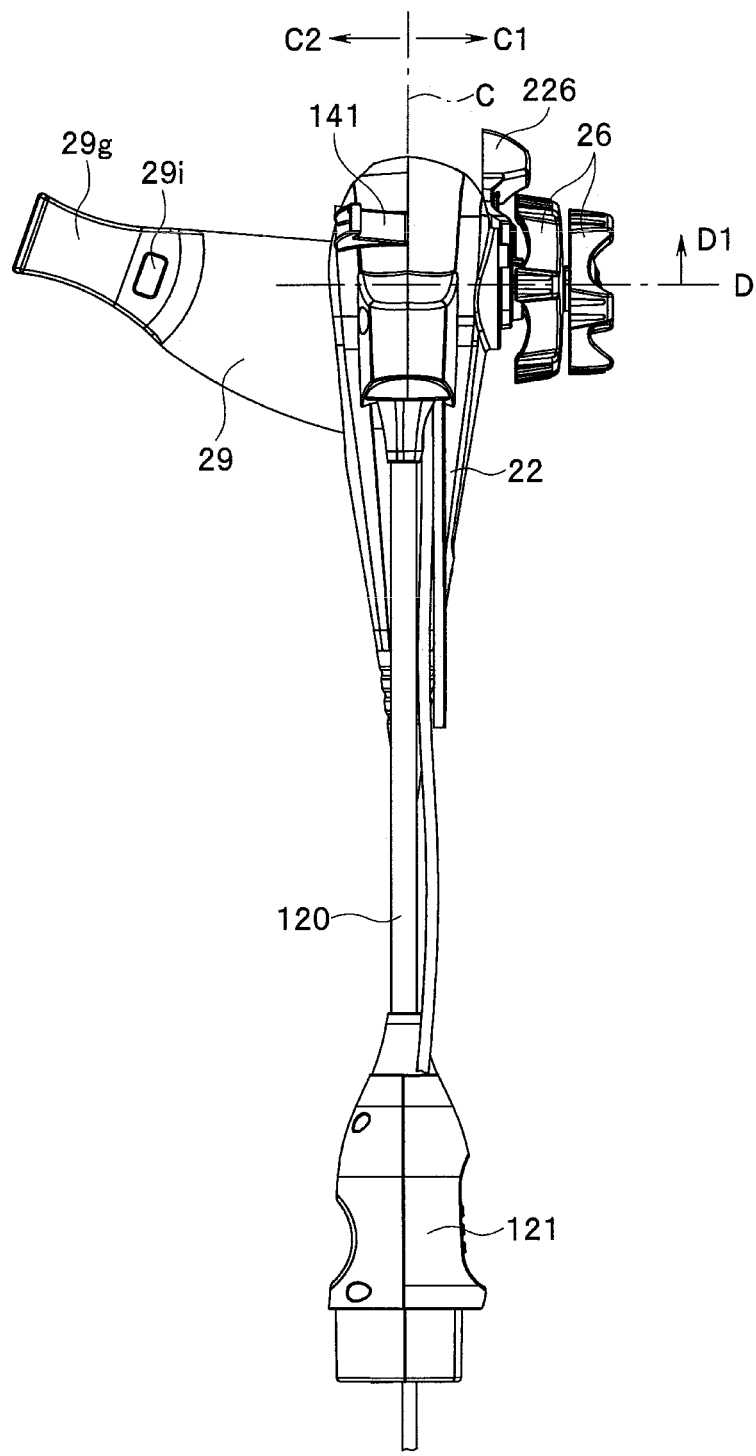
FIG. 13 is a side view of the baby endoscope shown in FIG. 11 as viewed in a direction XIII in FIG. 11.
Figure 14:
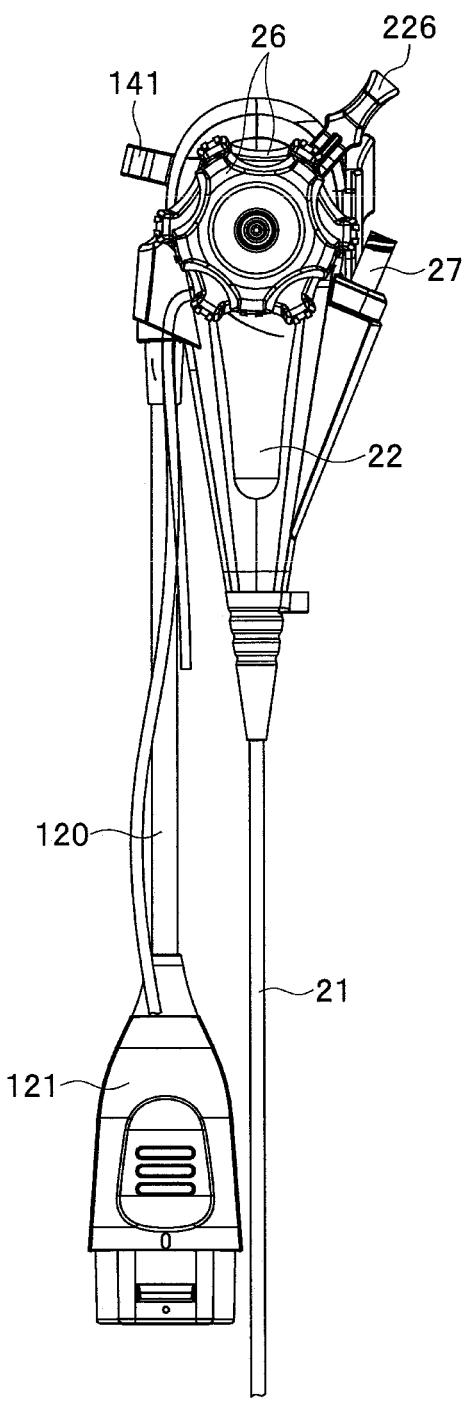
FIG. 14 is a front view of the baby endoscope shown in FIG. 11 as viewed in a direction XIV in FIG. 11.

FIG. 11 is an enlarged perspective view of the baby endoscope shown in FIG. 2. FIG. 12 is a side view of the baby endoscope shown in FIG. 11 as viewed in a direction XII in FIG. 11. FIG. 13 is a side view of the baby endoscope shown in FIG. 11 as viewed in a direction XIII in FIG. 11. FIG. 14 is a front view of the baby endoscope shown in FIG. 11 as viewed in a direction XIV in FIG. 11.

Figure 15:
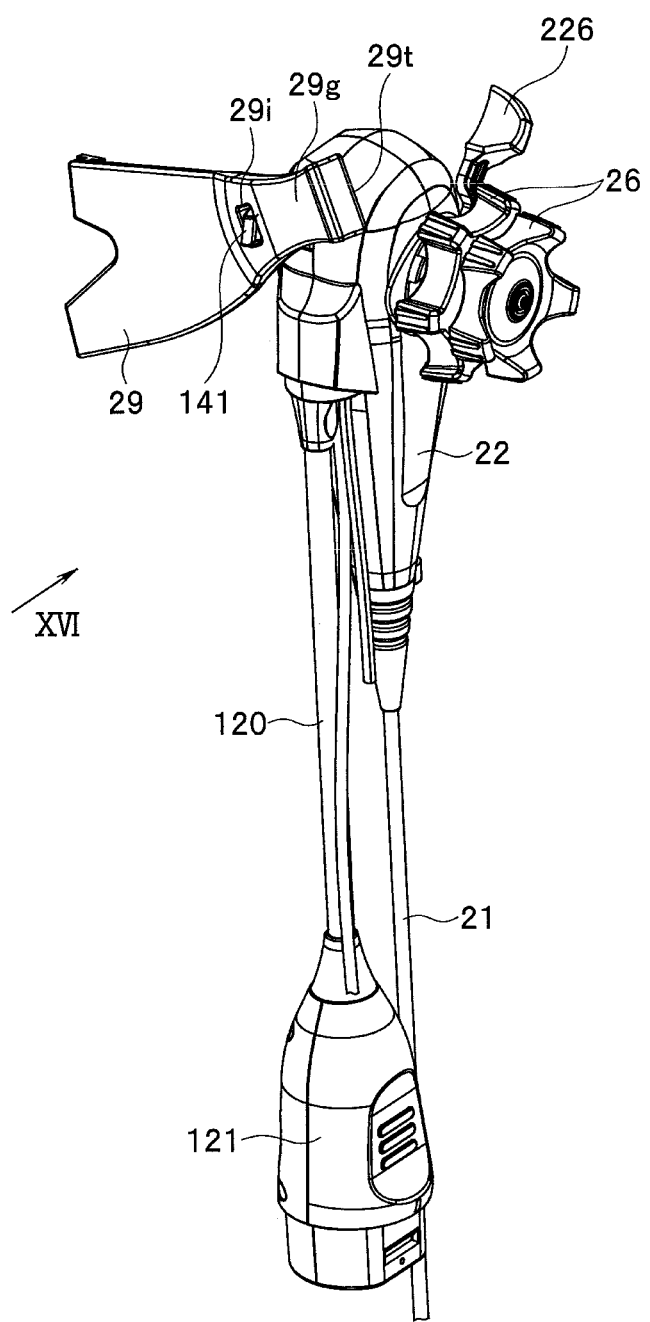
FIG. 15 is a perspective view showing a state where a hole of a fixing band is locked to a fixing band hook provided on the baby endoscope shown in FIG. 11.
Figure 16:
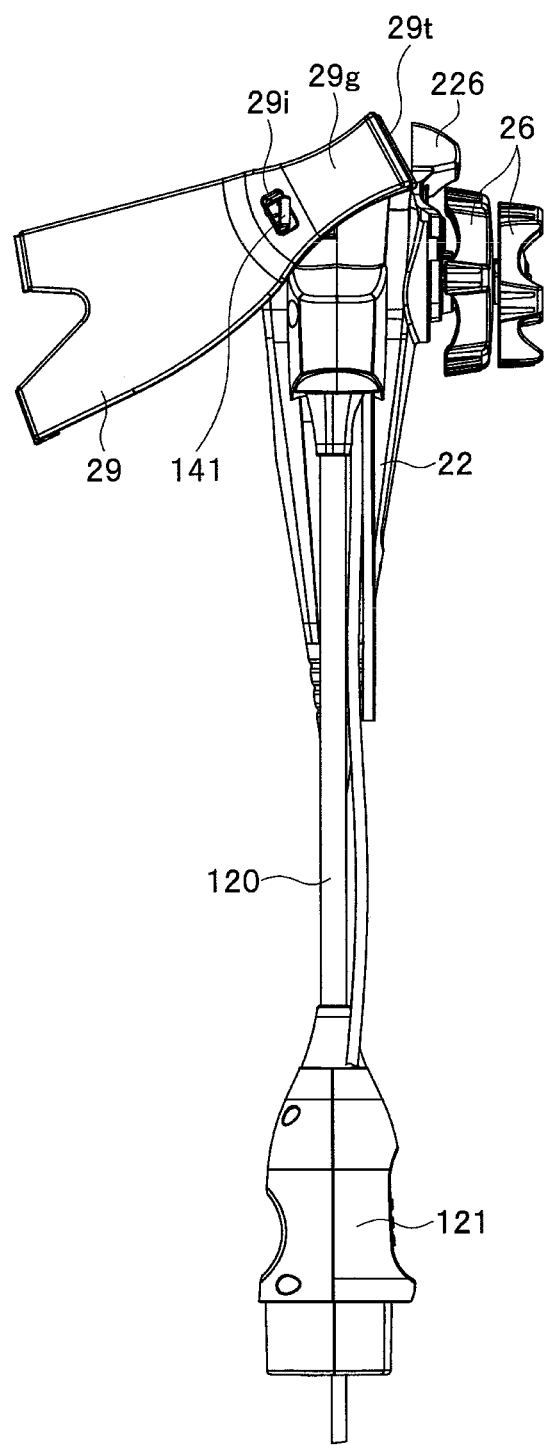
FIG. 16 is a side view of the baby endoscope shown in FIG. 15 as viewed in a direction XVI in FIG. 15.

FIG. 15 is a perspective view showing a state where a hole of the fixing band is locked to the fixing band hook provided on the baby endoscope shown in FIG. 11. FIG. 16 is a side view of the baby endoscope shown in FIG. 15 as viewed in a direction XVI in FIG. 15.

Figure 17:
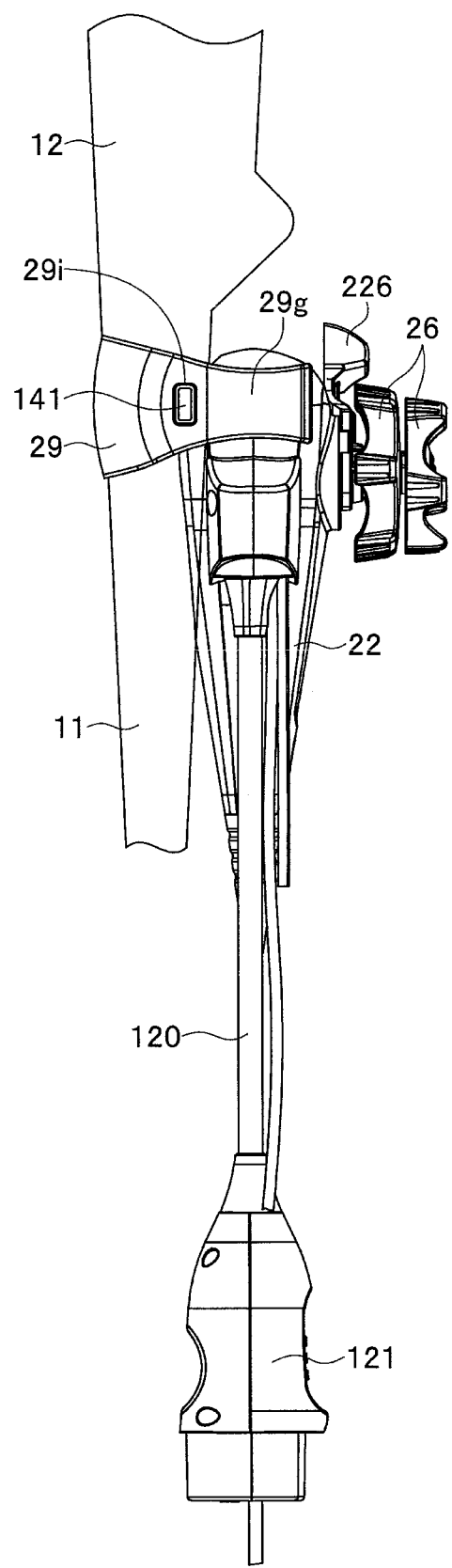
FIG. 17 is a partial side view showing a state where the operation portion of the baby endoscope shown in FIG. 11 is fixed to an operation portion of a mother endoscope by the fixing band.
Figure 18:
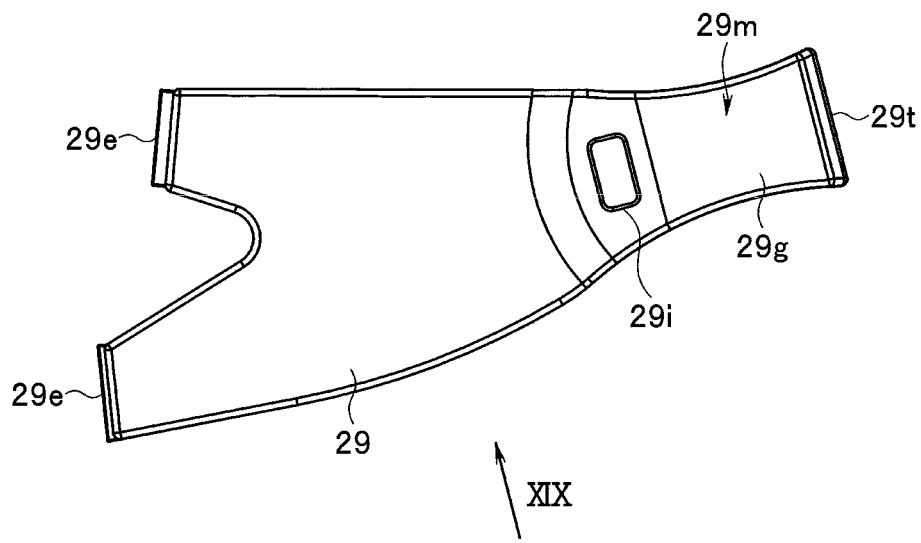
FIG. 18 is an enlarged plan view of the fixing band used for fixing the baby endoscope shown in FIG. 11.
Figure 19:
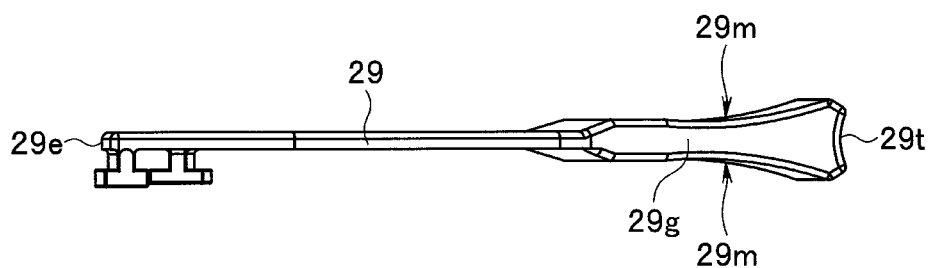
FIG. 19 is a side view of the fixing band shown in FIG. 18 as viewed in a direction XIX in FIG. 18.

FIG. 17 is a partial side view showing a state where the operation portion of the baby endoscope shown in FIG. 11 is fixed to the operation portion of the mother endoscope by the fixing band. FIG. 18 is an enlarged plan view of the fixing band used for fixing the baby endoscope shown in FIG. 11. FIG. 19 is a side view of the fixing band shown in FIG. 18 as viewed in a direction XIX in FIG. 18.

Hereinafter, the following configuration will be described as an example. The baby endoscope 20 shown in FIG. 11 to FIG. 17 differs from the baby endoscope 20 described in the above-mentioned present embodiment. In the baby endoscope 20 shown in FIG. 11 to FIG. 17, the cables/tubes 28 do not directly extend from the operation portion 22 but are inserted through a universal cord 120 and an endoscope connector 121, the universal cord 120 extending from the operation portion 22, the endoscope connector 121 being provided at an extension end of the universal cord 120.

In fixing the operation portion 22 of the baby endoscope 20 to the operation portion 12 of the mother endoscope 10 as shown in the above-mentioned FIG. 2, first, an operator pushes a pressing surface of the operation portion 22 on a side opposite to a surface to which the bending operation knobs 26 are provided against a surface to be pressed of the operation portion 12 to which the bending operation knobs 18 are provided.

At this point of operation, the surface to be pressed of the operation portion 12 is formed into a concave shape and the pressing surface of the operation portion 22 is formed into a convex shape, thus ensuring a large contact area at the time of pressing.

Next, the operator winds the fixing band 29 around the operation portion 12 and causes a hole 29i (see FIG. 11) formed at the other end 29t side (see FIG. 18) of the fixing band 29 to be locked to the fixing band hook 141 provided on the operation portion 12. Each one end 29e (see FIG. 18) of the fixing band 29 is fixed to a treatment instrument insertion pipe sleeve 27 side of the operation portion 22.

With such operations, the operation portion 22 is fixed to the operation portion 12 by the fixing band 29.

However, the operator generally performs fixing work in a state of wearing gloves. Therefore, there is a problem that when the hole 29i of the fixing band 29 is locked to the fixing band hook 141, a portion of the gloves may be caught by a locking portion, thus preventing the fixing work from being smoothly performed.

For this reason, there has been a demand for a configuration where the hole 29i of the fixing band 29 can be easily locked to the fixing band hook 141 with high workability.

In a configuration of the baby endoscope 20 shown in FIG. 11 to FIG. 19, a large finger grasping portion 29g to be grasped by fingers of the operator is provided on the other end 29t side of the fixing band 29.

To improve ease of grasping the finger grasping portion 29g with the fingers of the operator, as shown in FIG. 18 and FIG. 19, a grasping surface 29m of the finger grasping portion 29g has a gently curved surface shape.

To further improve ease of grasping the finger grasping portion 29g, fine stepped portions may be formed on the grasping surface 29m or a non-slip treatment, such as a coating, may be applied to the grasping surface 29m.

As shown in FIG. 18, the hole 29i is formed to be offset toward the one end 29e relative to the finger grasping portion 29g.

Conventionally, the hole 29i is formed at a position of the finger grasping portion 29g. In the present configuration, the hole 29i is located at a position offset toward the one end 29e relative to a position of a conventional hole, and the finger grasping portion 29g is a dedicated portion to be grasped by the fingers of the operator.

Conventionally, the hole 29i is formed at the position of the finger grasping portion 29g. Therefore, when an operator causes the hole 29i to be locked to the fixing band hook 141, the operator holds a portion where the hole 29i is formed and hence, there is a high possibility that a glove is caught by a locking portion (between the hole 29i and the fixing band hook 141).

In contrast, in the present configuration, the hole 29i is formed at a position offset relative to the finger grasping portion 29g. Therefore, an operator can easily and simply perform work to cause the hole 29i to be locked to the fixing band hook 141 by grasping the finger grasping portion 29g, without a glove being caught by the locking portion.

As shown in FIG. 13, the fixing band hook 141 is located at a position on a C2 side of a center axis C of the operation portion 22. The C2 side is opposite to a C1 side where the bending operation knobs 26 and the treatment instrument insertion pipe sleeve 27 are provided. Further, the fixing band hook 141 is located at a position above a center axis D of the bending operation knobs 26, that is, at a position on a D1 side (a side opposite to the insertion portion 21 of the operation portion 22) of the center axis D of the bending operation knobs 26.

With such a configuration, as shown in FIG. 15 and FIG. 16, in causing the hole 29i to be locked to the fixing band hook 141, even when the finger grasping portion 29g is formed on the fixing band 29, in other words, even when the hole 29i is formed to be offset toward the one end 29e relative to the finger grasping portion 29g as described above, there is no possibility that the finger grasping portion 29g and the other end 29t come into contact with the bending operation knob 26, a bending locking lever 226, or the like after the hole 29i is locked to the fixing band hook 141.

Further, due to the configuration where the hole 29i is locked to the fixing band hook 141 on the C2 side, different from a configuration where the hole 29i is locked to the fixing band hook 141 on the C1 side, there is no possibility that a locking position interferes with the treatment instrument insertion pipe sleeve 27.

Therefore, although the fixing band 29 is used for fixing the baby endoscope 20, the operation of the baby endoscope 20 can be comfortably performed.

Accordingly, it is possible to provide the configuration of the baby endoscope 20 shown in FIG. 17 where, in causing the hole 29i to be locked to the fixing band hook 141 to fix the operation portion 22 to the operation portion 12 by using the fixing band 29, it is possible to prevent a glove from being caught by the locking portion and to prevent the fixing band 29 from interfering with the bending operation knob 26, the bending locking lever 226, or the like of the operation portion 22.

Assume a case where the insertion portion 21 of the baby endoscope 20 is removed from the treatment instrument channel of the mother endoscope 10 and another treatment instrument is inserted into the treatment instrument channel from the treatment instrument insertion portion 16 in a state where the operation portion 22 of the baby endoscope 20 is fixed to the operation portion 12 of the mother endoscope 10 by using the fixing band 29 as described above. In such a case, since the operation portion 22 is fixed to the operation portion 12, it is impossible to move the baby endoscope 20 to another place unless the fixing of the baby endoscope 20 is released.

Therefore, in a state where the baby endoscope 20 is fixed to the mother endoscope 10, to keep the insertion portion 21 clean after the insertion portion 21 is removed, it is necessary to cause the insertion portion 21 to be grasped by a person other than the operator or to release the fixing of the baby endoscope 20 to move the insertion portion 21 to a place where the insertion portion 21 can be held in a clean state. For this reason, there is a problem that work is complicated.

Hereinafter, the description will be made with reference to FIG. 20 to FIG. 24 for a configuration which allows the insertion portion 21 of the baby endoscope 20 removed from the treatment instrument channel of the mother endoscope 10 to be easily and simply held in a clean state in the state where the baby endoscope 20 is fixed to the mother endoscope 10.

Figure 20:
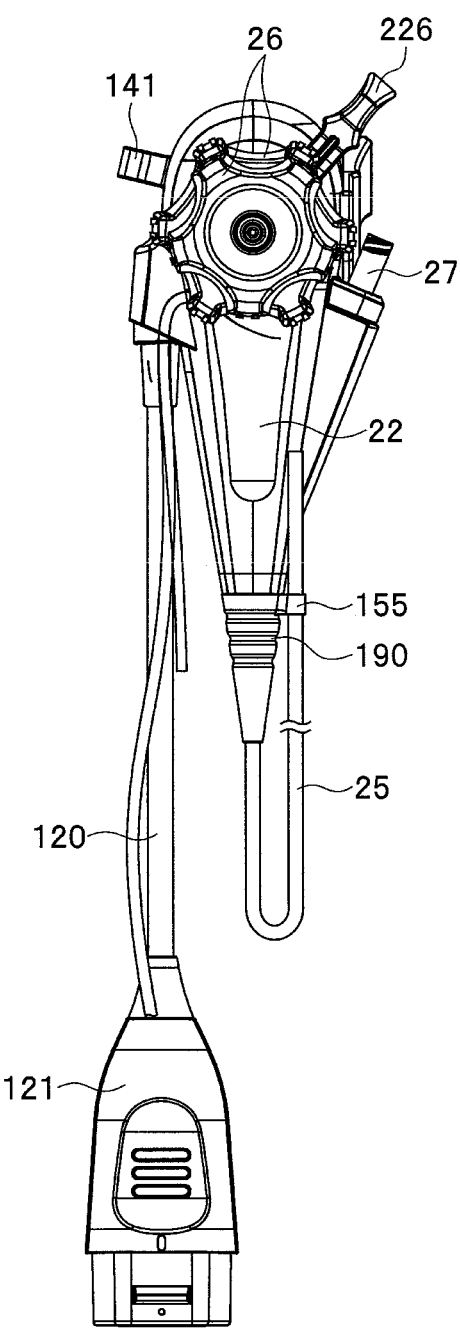
FIG. 20 is a plan view showing a configuration where an insertion portion holder is provided in the vicinity of a bend preventing portion of the operation portion of the baby endoscope shown in FIG. 14.
Figure 21:
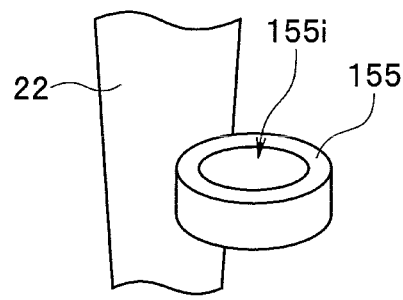
FIG. 21 is a perspective view showing the insertion portion holder shown in FIG. 20 in an enlarged manner together with a portion of the operation portion.

FIG. 20 is a plan view showing a configuration where an insertion portion holder is provided in the vicinity of a bend preventing portion of the operation portion of the baby endoscope shown in FIG. 14. FIG. 21 is a perspective view showing the insertion portion holder shown in FIG. 20 in an enlarged manner together with a portion of the operation portion.

Figure 22:
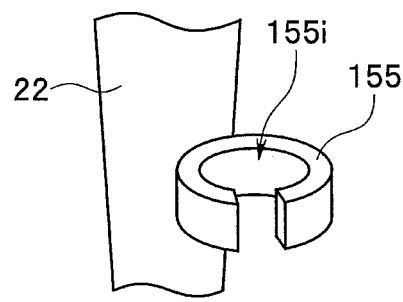
FIG. 22 is a perspective view showing a modification of a shape of the insertion portion holder shown in FIG. 21 together with the portion of the operation portion.
Figure 23:
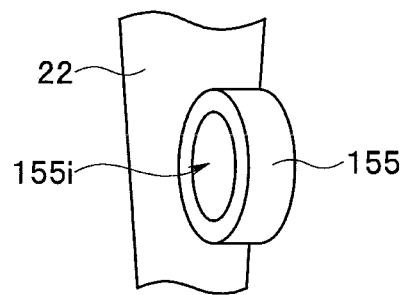
FIG. 23 is a perspective view showing another modification of the shape of the insertion portion holder shown in FIG. 21 together with the portion of the operation portion.
Figure 24:
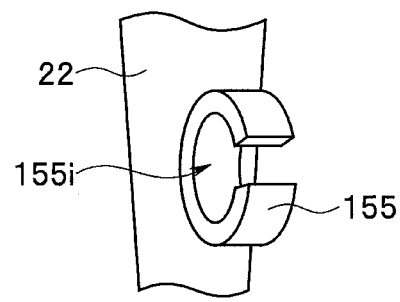
FIG. 24 is a perspective view showing still another modification of the shape of the insertion portion holder shown in FIG. 21 together with the portion of the operation portion.

FIG. 22 is a perspective view showing a modification of a shape of the insertion portion holder shown in FIG. 21 together with the portion of the operation portion. FIG. 23 is a perspective view showing another modification of the shape of the insertion portion holder shown in FIG. 21 together with the portion of the operation portion. FIG. 24 is a perspective view showing still another modification of the shape of the insertion portion holder shown in FIG. 21 together with the portion of the operation portion.

As shown in FIG. 20, an insertion portion holder 155 is provided in the vicinity of a bend preventing portion 190 of the operation portion 22 of the baby endoscope 20.

As shown in FIG. 21, the insertion portion holder 155 is formed into a ring shape having a hole 155i in which the insertion portion 21 is fitted.

As shown in FIG. 22, the insertion portion holder 155 may be formed into a C shape, or as shown in FIG. 23, the insertion portion holder 155 may be formed into a ring shape and provided to face in a direction different from a direction of the insertion portion holder 155 shown in FIG. 21 by approximately 90°. Alternatively, as shown in FIG. 24, the insertion portion holder 155 may be formed into a C shape and provided to face in a direction different from a direction of the insertion portion holder 155 shown in FIG. 22 by approximately 90°. Provided that the insertion portion holder 155 is a shape that can hold the insertion portion 21, the shape of the insertion portion holder 155 is not limited to these shapes.

With such a configuration, merely by fitting the insertion portion 21 removed from the treatment instrument channel of the mother endoscope 10 into the hole 155i of the insertion portion holder 155, it is possible to hold the insertion portion 21 in a clean state by preventing falling of the insertion portion 21 without releasing the fixing and without requiring another person to hold the insertion portion 21 even in a state where the baby endoscope 20 is fixed to the mother endoscope 10.

When the insertion portion 21 is in a held state by using the insertion portion holder 155, a holding position is in the vicinity of the operation portion 22 and hence, it is possible to achieve ease of operation when the insertion portion 21 is inserted into the treatment instrument channel of the mother endoscope 10 again.

Figure 25:
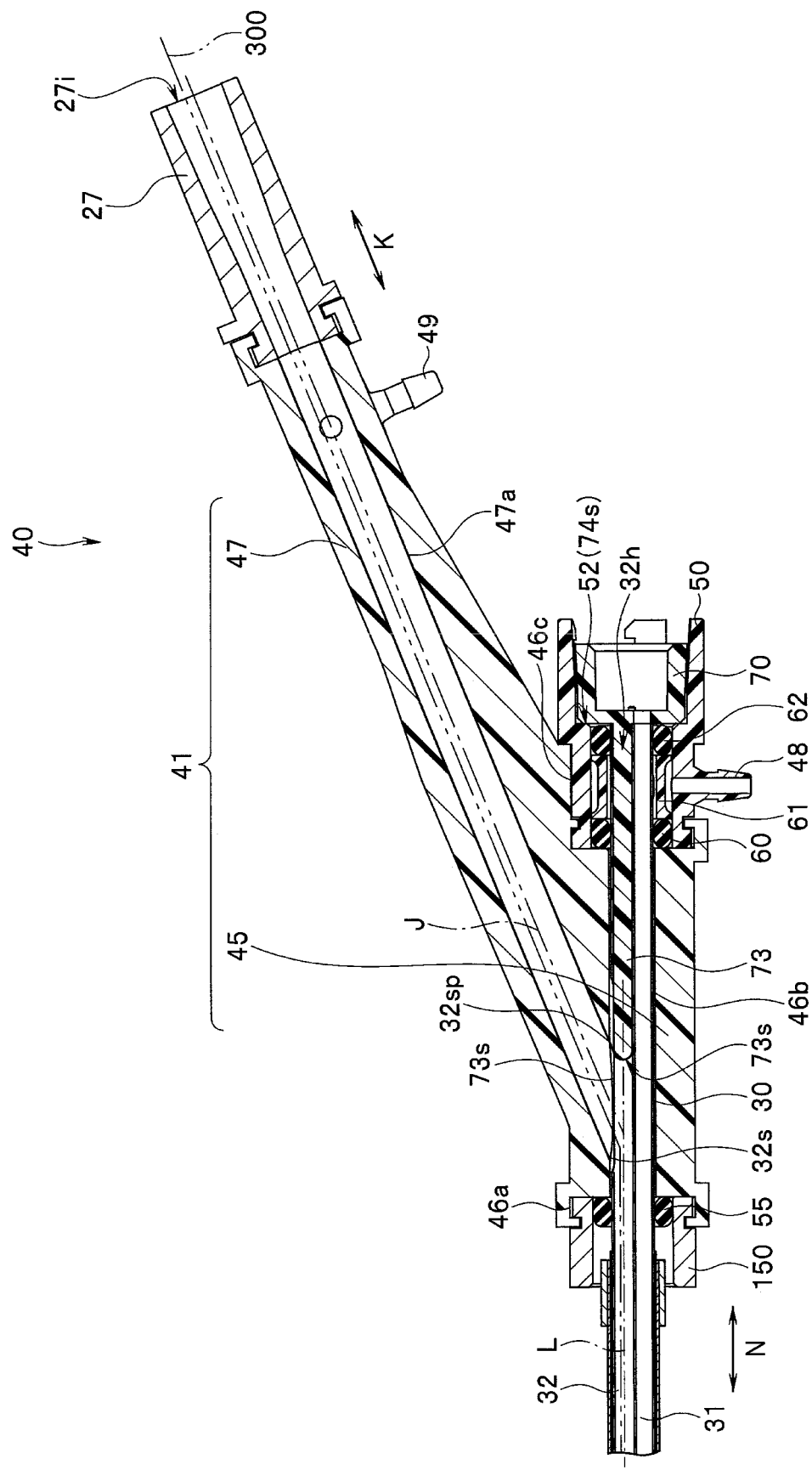
FIG. 25 is a cross-sectional view of a tube module showing a modification where a distal end surface of a sealing member shown in FIG. 8 is formed into a hemispherical shape.

Hereinafter, a modification is described with reference to FIG. 25. FIG. 25 is a cross-sectional view of a tube module showing the modification where a distal end surface of the sealing member shown in FIG. 8 is formed into a hemispherical shape.

As shown in FIG. 25, the distal end surface 73s of the sealing member 73 may be formed into a hemispherical shape, and the distal end surface 73s may be positioned at least at a position closer to the distal end side than the proximal end 32sp of the communication hole 32s.

With such a configuration, when the guide wire 300 is inserted into the channel hole 32 from the distal end side toward the proximal end side causing the guide wire 300 to enter the forceps channel 47a via the communication hole 32s, depending on a thickness of the guide wire 300 or a shape of a distal end of the guide wire 300, it is possible to smoothly guide the guide wire 300 to the forceps channel 47a from the channel hole 32 due to the distal end surface 73s having a hemispherical shape and being positioned at a position closer to the distal end side than the proximal end 32sp of the communication hole 32s. Other effects are equal to the effects of the above-mentioned present embodiment.

What is claimed is:

1. An endoscope comprising:
    an operation portion comprising:
        a tube having a first channel and a communication hole on an outer circumferential surface of the tube, the communication hole communicating with the first channel;
        a frame body having a second channel and a third channel, the tube being inserted into the second channel, the third channel communicating with the first channel via the communication hole; and
        a closing body configured to close a proximal opening of the first channel, the closing body having a distal end surface positioned distally relative to a proximal end of the communication hole.

2. The endoscope according to claim 1, wherein the distal end surface of the closing body is smoothly connected to the first channel and the third channel.

3. The endoscope according to claim 1, wherein a center axis of the third channel forms an acute angle with a center axis of the second channel.

4. The endoscope according to claim 3, wherein a portion of the distal end surface of the closing body is formed parallel to the center axis of the third channel.

5. The endoscope according to claim 1, wherein
    a portion of the distal end surface of the closing body and a longitudinal axis of the tube forms a first angle,
    a center axis of the third channel and the longitudinal axis forms a second angle, and
    the first angle is smaller than the second angle.

6. The endoscope according to claim 1, wherein the first channel is one of a plurality of channels formed in the tube.

7. The endoscope according to claim 1, wherein the closing body includes a locking portion locked to the frame body.

8. The endoscope according to claim 1, wherein the distal end surface, the first channel and the third channel form a curved surface.

9. The endoscope according to claim 1, wherein the distal end surface is formed into a hemispherical shape.

10. The endoscope according to claim 1, further comprising:
   an insertion portion provided distally relative to the operation portion,
   wherein a part of the tube is provided in the insertion portion.

11. The endoscope according to claim 1, wherein the distal end surface is exposed to the third channel through the communication hole.

12. The endoscope according to claim 1, wherein an entirety of a distal-most face of the distal end surface is positioned distally relative to the proximal end of the communication hole.

13. The endoscope according to claim 12, wherein the distal-most face has an inclined flat surface inclined relative to a longitudinal axis of the tube.

14. The endoscope according to claim 1, wherein the closing body is inserted into the first channel of the tube.

15. The endoscope according to claim 1, wherein the distal end surface has an inclined flat surface inclined relative to a longitudinal axis of the tube.

16. The endoscope according to claim 1, wherein a distal end of the distal end surface is positioned proximally relative to a distal end of the communication hole.

17. The endoscope according to claim 1, further comprising a seal provided between the outer surface of the tube and an inner surface of the second channel.

18. The endoscope according to claim 1, wherein the distal end surface has an elliptical shape.

19. The endoscope according to claim 1, wherein the closing body extends from the proximal end of the communication hole to a proximal end of the tube.

* * * * *